US012638409B2

(12) United States Patent
Alenezy et al.

(10) Patent No.: US 12,638,409 B2
(45) Date of Patent: May 26, 2026

(54) CHEMIRESISTIVE SUBSTRATE FOR A HYDROGEN GAS SENSOR

(71) Applicant: ROYAL MELBOURNE INSTITUTE OF TECHNOLOGY, Melbourne (AU)

(72) Inventors: Ebtsam Khalefah Alenezy, Al-Qurayyat (SA); Yilas Mohammad Sabri, Cranbourne East (AU); Ahmad Esmaiel Kandjani, Sunbury (AU); Samuel James Ippolito, Brunswick West (AU); Suresh Kumar Bhargava, Viewbank (AU)

(73) Assignee: ROYAL MELBOURNE INSTITUTE OF TECHNOLOGY, Melbourne (AU)

( * ) Notice: Subject to any disclaimer, the term of this patent is extended or adjusted under 35 U.S.C. 154(b) by 253 days.

(21) Appl. No.: 18/251,053

(22) PCT Filed: Oct. 29, 2021

(86) PCT No.: PCT/AU2021/051274
§ 371 (c)(1),
(2) Date: Apr. 28, 2023

(87) PCT Pub. No.: WO2022/087683
PCT Pub. Date: May 5, 2022

(65) Prior Publication Data
US 2023/0408475 A1    Dec. 21, 2023

(30) Foreign Application Priority Data
Oct. 30, 2020    (AU) ................................ 2020903952

(51) Int. Cl.
*G01N 27/12*        (2006.01)
*G01N 33/00*        (2006.01)

(52) U.S. Cl.
CPC ........... *G01N 27/125* (2013.01); *G01N 27/12* (2013.01); *G01N 27/127* (2013.01); *G01N 27/128* (2013.01); *G01N 33/005* (2013.01)

(58) Field of Classification Search
CPC ...... G01N 33/005; G01N 27/04; G01N 27/12; G01N 27/125; G01N 27/127; G01N 27/128; G01N 27/227
See application file for complete search history.

(56) References Cited

U.S. PATENT DOCUMENTS

2005/0224779 A1*  10/2005  Wang ................... H10D 62/118
                                                  257/E29.094
2013/0202489 A1    8/2013  Ong et al.
(Continued)

FOREIGN PATENT DOCUMENTS

CN        106198644 A    12/2016
CN        109813768 A     5/2019
(Continued)

OTHER PUBLICATIONS

International Search Report for corresponding application PCT/AU2021/051274 dated Nov. 15, 2021.
(Continued)

*Primary Examiner* — Paul M. West
(74) *Attorney, Agent, or Firm* — Norris McLaughlin, PA

(57) ABSTRACT
The invention provides a chemiresistive substrate for a dihydrogen-sensitive amperometric gas sensor, the chemiresistive substrate comprising: a crystalline semiconductive metal oxide layer comprising an array of spaced apart hollow metal oxide micro-shells protruding from a base plane of the metal oxide layer; and metallic nanoparticles decorating the metal oxide layer.

19 Claims, 15 Drawing Sheets

(56)     References Cited

U.S. PATENT DOCUMENTS

| 2016/0041116 | A1 |   | 2/2016 | Kim et al. |
| 2016/0334359 | A1 |   | 11/2016 | Kim et al. |
| 2017/0269043 | A1 | * | 9/2017 | Homma ............... G01N 33/005 |

FOREIGN PATENT DOCUMENTS

| CN | 110642288 | A |   | 1/2020 |
| KR | 101400605 | B1 |   | 5/2014 |
| KR | 20150051249 | A |   | 5/2015 |
| KR | 20150051249 | A1 |   | 5/2015 |
| KR | 101551539 | B1 | * | 9/2015 |
| WO | 2020178203 | A1 |   | 9/2020 |
| WO | 2022109684 | A1 |   | 6/2022 |

OTHER PUBLICATIONS

Li, et al., "Resistive type hydrogen gas sensor based on TiO2: A review", International Journal of Hydrogen Energy, 43 (2018), 21114-21132. (DOI: https://doi.org/10.1016/j.ijhydene.2018.09.051).

Chao, et al., "Amperometric sensor for selective and stable hydrogen measurement", Sensors and Actuators B 106 (2005) 784-790. (DOI: 10.1016/j.snb.2004.09.042).

Li, et al., "Highly sensitive and selective room-temperature formaldyhyde sensors using hollow TiO2 microspheres", Sensors and Actuators B 219 (2015) 158-163. (DOI: http://dx.doi.org/10.1016/j.snb.2015.05.031).

CN Search Report and English translation in corresponding application CN 2021800862552 dated Nov. 27, 2025.

* cited by examiner

CHEMIRESISTIVE SUBSTRATE FOR A HYDROGEN GAS SENSOR

This is an application filed under 35 USC 371 based on PCT/AU2021/051274 filed 29 Oct. 2021, which claimed priority to AU 2020903952 filed 30 Oct. 2020. The present application claims the full priority benefit of all prior applications and incorporates by reference their full disclosures as if set forth herein.

TECHNICAL FIELD

The invention relates to a chemiresistive substrate for a dihydrogen-sensitive amperometric gas sensor. The chemiresistive substrate comprises a crystalline semiconductive metal oxide layer comprising an array of spaced apart hollow metal oxide micro-shells protruding from a base plane of the metal oxide layer, and metallic nanoparticles decorating the metal oxide layer. The invention also relates to an amperometric gas sensor for detecting dihydrogen, a system for detecting dihydrogen in an oxygen-containing gas, a method of detecting dihydrogen in an oxygen-containing gas, and a method of producing a dihydrogen-sensitive chemiresistive substrate.

BACKGROUND OF INVENTION

Hydrogen gas (dihydrogen, $H_2$) is widely used in industrial environments and is increasingly attractive in transportation and distributed power applications (e.g. fuel cells) as a non-polluting carrier of renewable energy. In environments where $H_2$ is used, $H_2$ sensors are often needed both for process control and safety monitoring. Sensitivity to low $H_2$ concentrations, with rapid sensor response times, is critical because of the high flame propagation velocity, low ignition energy, and wide explosive envelope of $H_2$.

The detection of low $H_2$ concentrations is also of interest in medical applications, for example in breath diagnostics where elevated $H_2$ concentrations (about 20 ppm) are associated with gastrointestinal diseases (GID) such as Irritable Bowel Syndrome (IBS).

Gas chromatography (GC) is one technique used to monitor and quantify low $H_2$ concentrations in gases. However, GC equipment is typically bulky, expensive and operator-intensive. The emerging use of $H_2$ in small-scale and distributed applications has incentivized the development of new $H_2$ detector systems which are cost-effective and simple to operate.

Solid-state sensors are particularly attractive because of their miniaturization and mass-production potential, simple operation, low power consumption, fast measurement capacity, portability and low cost. Such sensors typically employ a chemiresistive substrate which interacts with $H_2$, the resistance of the substrate being correlated to the $H_2$ concentration. The resistance can be measured directly (a chemiresistive sensor), or a fixed potential difference is established across the substrate and the current response is measured (an amperometric gas sensor, or AGS).

Because the input potential can itself alter the electrical properties of the chemiresistive substrate and thus the gas absorption chemistry, AGS devices can be tailored for improved selectivity towards a target species by controlling both the substrate composition/morphology and by operating the device at an applied potential which thermodynamically favours the redox reaction of the target species. In the case of $H_2$ detection, the redox reaction of interest is surface-catalysed oxidation of $H_2$ to water.

Gas sensors with $H_2$-sensitive chemiresistive substrates have previously been reported, typically employing a semiconductor metal oxide such as titanium dioxide ($TiO_2$), zinc oxide (ZnO), tungsten trioxide ($WO_3$) or and tin dioxide ($SnO_2$). High surface area morphologies are generally required to provide good sensitivity, for example using nanoparticulate $TiO_2$ (e.g. nanofiber membranes) or anodised substrates comprising vertically aligned $TiO_2$ nanotubes. In some cases, the semiconductor surface has been functionalised with metals capable of facilitating $H_2$ chemisorption and dissociation on the substrate surface.

Despite their theoretical advantages, metal-oxide based AGS systems typically suffer from one or more significant difficulties in practice, particularly for low concentration $H_2$ detection. To provide the high surface areas necessary for good sensitivity, micro-structured chemiresistive layers for some AGS sensors have been produced by assembling pre-existing metal oxide particles into an interconnected network over the sensor electrodes. However, the baseline resistivity of such a layer is highly dependent on the particle morphology and the junctions created between adjacent particles in the network. This can lead to divergent chemiresistive properties in different parts of the chemiresistive substrate, to the extent that some sections may be electrically isolated. Moreover, poor reproducibility may be obtained between different sensors, despite being produced by ostensibly the same production method, so that each sensor may need to be individually calibrated.

Aside from the irreproducibility of the chemiresistive response, both across the surface of a single substrate and between substrates, due to morphological irregularity and inter-particle junction effects, other shortcomings of metal oxide sensors include the lack of selectivity towards $H_2$ and the high temperature of operation required. The catalysed reaction of $H_2$ and $O_2$ on a semiconductor-based chemiresistive substrate relies on electrons excited to the conduction band of the metal oxide. At low temperatures (e.g. below 140° C.), there is insufficient energy to promote electrons across the band gap and the sensitivity of the substrate is low.

Another method to overcome the activation barrier and increase sensitivity at low temperature is optical excitation, i.e. illuminating the chemiresistive substrate with light (e.g. UV light) having an energy greater than the semiconductor band gap. In this case, it is particularly important that the chemiresistive substrate of the sensor exhibits a high degree of uniformity in its surface morphology. Uncontrolled variation in the surface microstructure, both in short-range topology (e.g. particle size and packing effects) and long-range order, can lead to variable photoresponse and thus a variable current response on different parts of the substrate. The structure and abundance of catalytically active surface sites, the optical stimulation received by different parts of the surface, and the inherent resistance through the bulk of the substrate, can all be affected.

As a result of their methods of production, previously reported $TiO_2$ based chemiresistive substrates generally exhibit surface layer morphologies with unsatisfactory short- and/or long-range uniformity. Thus, AGS devices comprising such substrates are not expected to provide good sensitivity at low $H_2$ concentrations (e.g. below 100 ppm) and/or low limits of detection (e.g. below 10 ppm), particularly when operated at low temperatures under optical stimulation.

There is therefore an ongoing need for chemiresistive substrates for a dihydrogen-sensitive amperometric gas sensor which at least partially address one or more of the above-mentioned short-comings, or provide a useful alternative.

A reference herein to a patent document or other matter which is given as prior art is not to be taken as an admission that the document or matter was known or that the information it contains was part of the common general knowledge as at the priority date of any of the claims.

SUMMARY OF INVENTION

The present invention relies in part on the development of a chemiresistive semiconductive metal oxide-based substrate with a highly uniform and reproducible surface morphology, despite exhibiting the high surface area required for $H_2$ sensing applications. This is achieved by providing a thin but generally continuous surface layer (or film) of crystalline semiconductor metal oxide on the sensor substrate, the layer including an array of spaced apart hollow metal oxide micro-shells which protrude from the substrate. The micro-structured metal oxide layer is decorated with metallic nanoparticles to facilitate $H_2$ chemisorption and dissociation. The composition and structure of the surface renders it suitable for use as a chemiresistive substrate for an AGS sensor.

When optically stimulated with UV light, an AGS device incorporating the chemiresistive substrate can provide excellent sensitivity to $H_2$ at low concentrations (linear response demonstrated in the range of 50-500 ppm), a very low limit of detection (as low as 3.5 ppm demonstrated) and high selectivity towards $H_2$ (demonstrated selectivity above 93% in the presence of a variety of confounding gas species, including water). Without limitation by theory, these results are attributed to the excellent short- and long-range uniformity in the surface morphology of the micro-structured $TiO_2$ substrate.

The desirable surface morphology of the chemiresistive substrate can be provided by a methodology involving preparation of a polymeric template on the substrate, chemical vapour deposition (CVD) of the metal oxide layer, calcination to remove the template and crystallise the metal oxide, and decoration of the metal oxide layer with the metallic nanoparticles. The resultant hollow hemispherical micro-shells are porous, which provides high surface area and enables gas molecules to interact with the substrate on the outside and inside of the hollow micro-shells. Notably, the high surface area morphology does not rely on the assembly of discrete, pre-existing metal oxide nano- or microparticles into a conductive network, such as a charge transferring sensing layer through particle deposition and agglomeration, but instead is achieved by depositing a continuous film of metal oxide. The methodology is reproducible and susceptible to large-scale and low-cost production, with the configuration and uniformity of the surface morphology provided by controlling well-defined production parameters. In particular, the method allows accurate control of the size and patterning of the polymeric particles in the template, which has been found critical to ensure that a highly uniform micro-structured layer of crystalline semiconductive metal oxide is subsequently formed.

In accordance with a first aspect the invention provides a chemiresistive substrate for a dihydrogen-sensitive amperometric gas sensor, the chemiresistive substrate comprising: a crystalline semiconductive metal oxide layer comprising an array of spaced apart hollow metal oxide micro-shells protruding from a base plane of the metal oxide layer; and metallic nanoparticles decorating the metal oxide layer.

The crystalline semiconductive metal oxide layer is generally a continuous film. A continuous film, for example as formed by chemical vapour deposition, can be distinguished from discontinuous and/or porous metal oxide layers of the type produced by assembling pre-existing and discrete metal oxide particles into a conductive network, for example in a layer arranged between interdigitated electrodes of a sensor. In embodiments, the crystalline semiconductive metal oxide layer is not formed by assembling pre-existing and discrete metal oxide particles into a layer. The micro-structuring and enhanced surface area of the crystalline semiconductive metal oxide layer is instead provided by the presence of the hollow metal oxide micro-shells (e.g. produced by colloidal templating), which are nevertheless an integral part of the continuous layer.

In some embodiments, the metal oxide is selected from the group consisting of titanium dioxide ($TiO_2$), zinc oxide (ZnO), tungsten trioxide ($WO_3$) and tin dioxide ($SnO_2$). In some embodiments, the metal oxide is titanium dioxide ($TiO_2$).

In some embodiments, the metallic nanoparticles comprise at least one metal selected from the group consisting of palladium, platinum, magnesium and nickel.

In some embodiments, the metal oxide micro-shells are substantially hemispherical.

In some embodiments, the metal oxide micro-shells have substantially uniform dimensions.

In some embodiments, the metal oxide micro-shells have a diameter in the range of 0.1 to 2 micrometers, such as in the range of 0.3 to 1.5 micrometers.

In some embodiments, the metal oxide micro-shells are spaced apart from their nearest neighbours by a distance of at least 0.2 micrometers, or a distance in the range of 0.2 to 2 micrometers, such as in the range of 0.3 to 1.5 micrometers.

In some embodiments, the metal oxide layer, absent the metallic nanoparticles, interacts with light in the range of 200 to 800 nm as a photonic crystal.

In some embodiments, the array is a substantially hexagonal array.

In some embodiments, the metal oxide layer has a thickness of between about 40 nm and about 100 nm, such as between about 50 nm and about 90 nm.

In some embodiments, the metal oxide layer is formed on a support surface.

In some embodiments, the metallic nanoparticles are Pd nanoparticles.

In some embodiments, the metallic nanoparticles are present on the metal oxide layer in an amount of between about 3 wt. % and about 15 wt. %, such as between about 5 wt. % and about 12 wt. %.

In accordance with a second aspect the invention provides an amperometric gas sensor for detecting dihydrogen, comprising: a pair of electrodes on a support surface; and a chemiresistive substrate according to any embodiment of the first aspect arranged over the electrodes on the support surface.

In accordance with a third aspect the invention provides a system for detecting dihydrogen in an oxygen-containing gas, the system comprising: an amperometric gas sensor according to any embodiment of the second aspect; a power supply to apply a potential difference between the electrodes; and a current meter to measure the current flowing between the electrodes through the chemiresistive substrate.

In some embodiments, the system further comprises a light source to illuminate the chemiresistive substrate of the amperometric gas sensor with light having an energy greater than the metal oxide band gap.

In accordance with a fourth aspect the invention provides a method of detecting dihydrogen in an oxygen-containing gas, the method comprising: exposing the chemiresistive substrate of an amperometric gas sensor according to any embodiment of the second aspect to a gas, wherein the gas is an oxygen-containing gas comprising hydrogen; applying a potential difference between the electrodes; and measuring the current flowing between the electrodes through the chemiresistive substrate.

In some embodiments, the potential difference is at least 3V, or at least 6V, such as about 9V.

In some embodiments, the method further comprises illuminating the chemiresistive substrate of the amperometric gas sensor with light having an energy greater than the metal oxide band gap.

In some embodiments, the chemiresistive substrate is maintained at a temperature of below 100° C., or below 50° C.

In some embodiments, the gas further comprises one or more contaminant gases, for example including one or more of water vapour, carbon dioxide, methyl ethyl ketone, acetone, acetaldehyde and nitric oxide.

In some embodiments, the gas comprises hydrogen in an amount of between 4 ppm and 4 vol %, such as between 4 ppm and 1000 ppm.

In some embodiments, the method further comprises determining the concentration of dihydrogen in the gas using a calibration curve which relates current response to hydrogen concentration.

In accordance with a fifth aspect the invention provides a method of producing a dihydrogen-sensitive chemiresistive substrate, the method comprising: producing a close-packed monolayer array of polymeric microspheres on a support surface; etching the polymeric microspheres to produce an array of spaced apart polymeric microparticles on the support surface; depositing a coating of metal oxide over the support surface and the polymeric microparticles; calcining the coated support surface to remove the polymeric microparticles and produce a crystalline semiconductive metal oxide layer on the support surface, the metal oxide layer comprising an array of spaced apart hollow metal oxide micro-shells protruding from a base plane of the metal oxide layer; and decorating the metal oxide layer with metallic nanoparticles.

In some embodiments, the metal oxide is selected from the group consisting of titanium dioxide ($TiO_2$), zinc oxide (ZnO), tungsten trioxide ($WO_3$) and tin dioxide ($SnO_2$). In some embodiments, the metal oxide is titanium dioxide ($TiO_2$).

In some embodiments, the metallic nanoparticles comprise at least one metal selected from the group consisting of palladium, platinum, magnesium and nickel.

In some embodiments, the microspheres are etched by plasma etching.

In some embodiments, the polymeric microspheres have a substantially uniform diameter in the range of 0.4 to 10 micrometers.

In some embodiments, the polymeric microparticles are spaced apart by at least 0.3 micrometers.

In some embodiments, the coating of metal oxide is deposited over the support surface and polymeric microparticles by chemical vapour deposition. In some embodiments, the chemical vapour deposition comprises hydrolysing a metal precursor compound, such as a metal alkyl or metal alkoxide, for example titanium isopropoxide, to produce a hydrolysed metal vapour, and contacting the support surface and polymeric microparticles with the hydrolysed metal vapour.

In some embodiments, the metal oxide layer has a thickness of between about 40 nm and about 100 nm, or between about 50 nm and about 90 nm.

In some embodiments, the metal oxide layer interacts with light in the range of 200 to 800 nm as a photonic crystal before decorating the metal oxide layer with the metallic nanoparticles.

In some embodiments, the metal oxide micro-shells have a diameter in the range of 0.1 to 2 micrometers, such as in the range of 0.3 to 1.5 micrometers.

In some embodiments, the metal oxide micro-shells are spaced apart from their nearest neighbours by a distance of at least 0.2 micrometers, or a distance in the range of 0.2 to 2 micrometers, such as in the range of 0.3 to 1.5 micrometers.

In some embodiments, decorating the metal oxide layer with metallic nanoparticles comprises contacting the metal oxide layer with an electroless bath solution comprising a metal salt and a reducing agent.

In some embodiments, seeding the metal oxide layer with reduced metal before contacting the metal oxide layer with the electroless bath solution.

In some embodiments, the metallic nanoparticles are Pd nanoparticles.

In some embodiments, the metallic nanoparticles are present on the metal oxide layer in an amount of between about 3 wt. % and about 15 wt. %, or between about 5 wt. % and about 12 wt. %.

In some embodiments, the support surface comprises a pair of electrodes, and the metal oxide layer is produced over the electrodes on the support surface In accordance with a sixth aspect the invention provides a dihydrogen-sensitive chemiresistive substrate, produced by a method according to the fifth aspect.

Where the terms "comprise", "comprises" and "comprising" are used in the specification (including the claims) they are to be interpreted as specifying the stated features, integers, steps or components, but not precluding the presence of one or more other features, integers, steps or components, or group thereof.

Further aspects of the invention appear below in the detailed description of the invention.

BRIEF DESCRIPTION OF DRAWINGS

Embodiments of the invention will herein be illustrated by way of example only with reference to the accompanying drawings in which.

DETAILED DESCRIPTION

Chemiresistive Substrate

Figure 1:
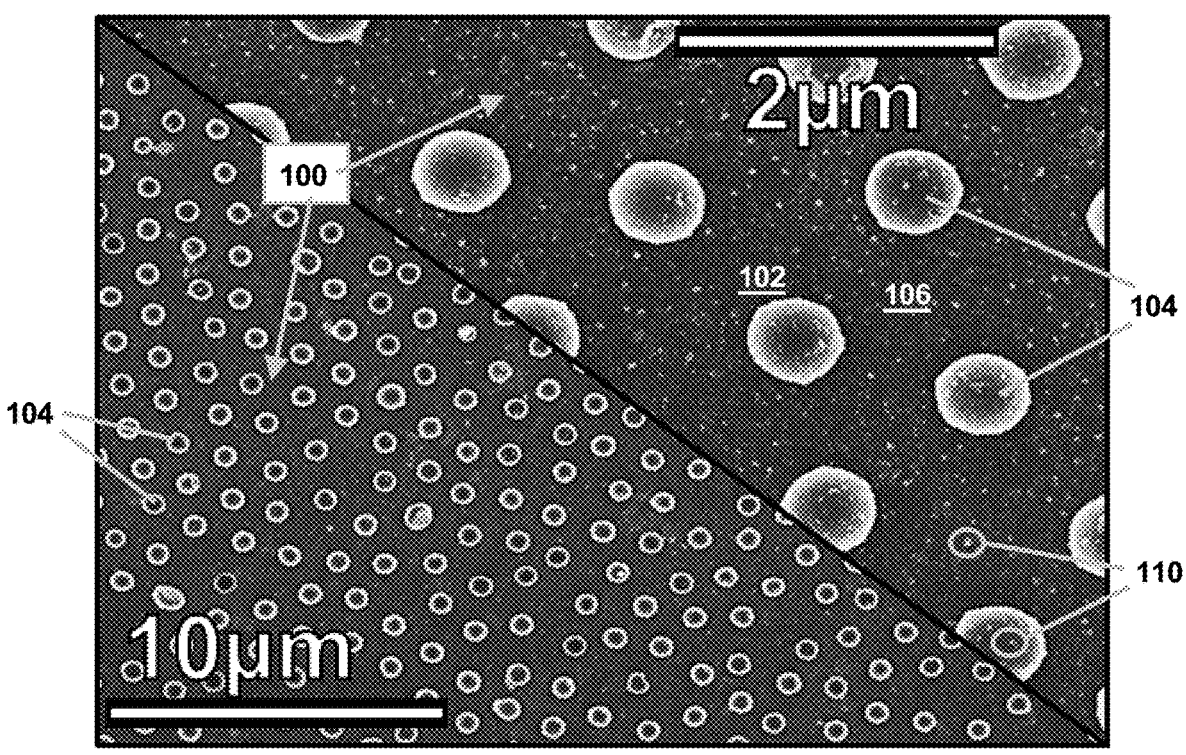
FIG. 1 depicts scanning electron microscope (SEM) images of a chemiresistive substrate according to an embodiment of the invention, as produced in Example 5.

The invention relates to a chemiresistive substrate for an amperometric gas sensor (AGS), in particular for a dihydrogen-sensitive AGS. The chemiresistive substrate comprises a crystalline semiconductive metal oxide layer comprising an array of spaced apart hollow metal oxide micro-shells protruding from a base plane of the metal oxide layer, and metallic nanoparticles decorating the metal oxide layer.

The metal oxide layer of the chemiresistive substrate is typically formed on a support surface of a mechanically stable substrate, which may include other conventional components of an AGS device such as a pair of electrodes, e.g. interdigitated electrodes, over which the metal oxide layer is formed. As will be explained in greater detail in subsequent sections, the metal oxide layer may be formed on the substrate by a multistep method which produces the highly uniform morphology of the chemiresistive substrate.

Crystalline Semiconductive Metal Oxide Layer

The chemiresistive substrate comprises a crystalline semiconductive metal oxide layer. A range of semiconductive metal oxides are reported to be capable of (photo)catalysing the reaction of $O_2$ and $H_2$ to form water, via a number of surface-adsorbed intermediate species. Without wishing to be bound by any theory, it is believed that the abundance of these surface-absorbed intermediate species on the semiconductive metal oxide affects its conductivity. The $H_2$ concentration dependent variation in the surface species provides the chemiresistive properties required for $H_2$ sensing, particularly when the metal oxide is a micro-structured material with a high surface-to-volume ratio. In particular, it has been proposed that $O_2$ reacts with conduction band electrons in the semiconductor to form surface oxygen ion species. These species then react further with hydrogen to form water. The surface concentration of the adsorbed oxygen ion species, which is sensitive to the $H_2$ concentration in the gas exposed to the substrate, thus determines the current response of the micro-structured semiconductor at a given process condition.

A range of different semiconductive transition metal oxides are reportedly suitable for dihydrogen sensing applications, and the metal oxide may be any of these materials. Suitable metal oxides include, but are not limited to, titanium dioxide ($TiO_2$), zinc oxide (ZnO), tungsten trioxide ($WO_3$) and tin dioxide ($SnO_2$). In some embodiments, the metal oxide is a wide band gap semiconductor. In some embodiments, the semiconductive metal oxide is $TiO_2$. Crystalline $TiO_2$ is an n-type semiconductor with wide band gap, for example about 3.2 eV for the anatase phase. Micro-structured $TiO_2$ is thus susceptible to photoactivation under UV light, resulting in charge separation of valence band holes and conduction band electrons which can surface-activate $O_2$ for reaction with hydrogen.

The crystalline semiconductive metal oxide layer is generally a thin and continuous film, for example having a thickness of between about 40 nm and about 100 nm, or between 50 nm and about 90 nm. Film thicknesses in this range have been found sufficiently robust to maintain the uniform morphology of the chemiresistive substrate, while still providing excellent sensitivity in $H_2$ sensing applications.

The crystalline semiconductive metal oxide layer comprises an array of spaced apart hollow metal oxide micro-shells protruding from a base plane of the metal oxide layer. This morphology, which may be provided by the preparation method described hereafter, provides a high surface area and excellent short- and long-range uniformity across the chemiresistive substrate surface.

Figure 2:
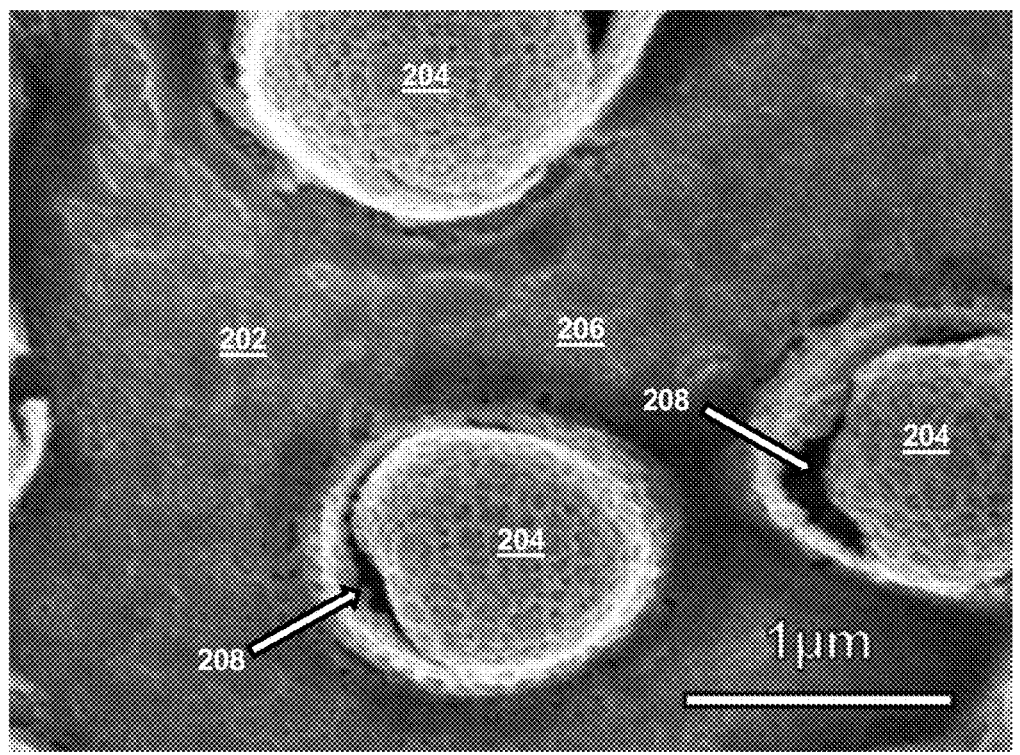
FIG. 2 depicts a SEM image of hollow and porous $TiO_2$ micro-shells on a crystalline $TiO_2$ layer, before it was decorated with metallic nanoparticles, as produced in Example 2.

The micro-structured metal oxide layer will now be described with reference to FIGS. 1 and 2. FIG. 1 depicts scanning electron microscope (SEM) images of chemiresistive substrate 100 according to an embodiment of the invention. FIG. 2 depicts a SEM image of hollow micro-shells 204 on a crystalline $TiO_2$ layer 200 before it was decorated with metallic nanoparticles.

Chemiresistive substrate 100 comprises crystalline $TiO_2$ thin film 102 formed on a planar support surface (not shown). $TiO_2$ thin film 102 includes an array of spaced apart, hollow $TiO_2$ micro-shells 104 which protrude from the base plane 106 of the film. The array of micro-shells 104 exhibits uniformity both in the size and shape of the individual micro-shells, and in the distribution of the micro-shells across the surface of chemiresistive substrate 100. As best seen in FIG. 2, micro-shells 204 are hollow and porous (as indicated by arrows 208), so that both the inside and outside surfaces of the $TiO_2$ micro-shells are exposed to a gas in contact with the substrate. It can also be seen in FIG. 2 that micro-shells 204 are integrally formed in $TiO_2$ layer 200, but protrude from the base plane 206 which is co-planar with the underlying support surface on which it is formed.

Although porous, the hollow micro-shells are generally enclosed shell-type structures with an enclosed interior volume defined by the micro-shell walls. In addition to the advantageous uniformity provided by the consistent dimensions of the micro-shells and their ordered arrangement over the substrate surface, the individual micro-shells themselves are thus structurally distinct from other micro-structured features such as nanoparticulates or open nanotubes, such as can be formed by anodisation of titanium substrates.

As used herein, the base plane of the crystalline semiconductive metal oxide layer refers to those regions of the layer which surround and space apart the micro-shells, and from which the micro-shells protrude. The base plane is typically in direct contact with the support surface on which the layer is formed, and thus adopts its shape. On a planar substrate, the base plane of the crystalline semiconductive metal oxide layer will thus also be approximately planar.

The metal oxide micro-shells may be substantially hemi-spherical in shape, and may have substantially uniform dimensions. In some embodiments, the metal oxide micro-shells have a size or diameter (e.g. in the plane of the layer) in the range of 0.1 to 2 micrometers, such as in the range of 0.3 to 1.5 micrometers. As will be explained hereafter, the size of the micro-shells can be determined by the initial and etched sizes of the microspheres used to template the metal oxide layer. It is thus envisaged that larger micro-shells can be produced by this approach, for example between 0.1 and 10 micrometers.

The micro-shells are spaced apart in the array, which means that they are not directly adjacent but are separated from each other by intermediate regions which form the base layer. This structure may ensure that the metal oxide layer is adequately adhered to and supported by the underlying support surface, thereby providing structural integrity to the chemiresistive substrate. In some embodiments, the metal oxide micro-shells are spaced apart from their nearest neighbours (rim to rim, across the intermediate base plane) by a distance of at least 0.2 micrometers, or a distance in the range of 0.2 to 2 micrometers, such as in the range of 0.3 to 1.5 micrometers.

The arrangement of the micro-shells in an array provides a measure of long-range uniformity in the surface configuration and surface area. In some embodiments, the array may comprise a periodic, i.e. substantially repeating, arrangement or pattern of the micro-shells on the surface. In such embodiments, the metal oxide layer, absent the metallic nanoparticles, may have properties of a photonic crystal, so that it interferes with or otherwise interacts with light, for example in the range of 200 to 800 nm wavelength.

In some embodiments, the metal oxide layer comprises a substantially hexagonal array of the micro-shells, at least over sections of the supporting surface. The configuration of the micro-shells thus approximates a hexagonal lattice (also known as a triangular lattice), with each micro-shell in the array having six nearest neighbours arranged hexagonally around it. However, it will be appreciated that in practice the positioning of micro-shells in a substantially hexagonal array may deviate from the geometrical precision of a mathematically perfect hexagonal lattice.

Metallic Nanoparticles

The crystalline semiconductive metal oxide layer of the chemiresistive substrate is decorated, i.e. surface-functionalised, with metallic nanoparticles. As used herein, a metallic nanoparticle is a nanoparticle, or metal cluster, comprising one or more metal elements which are substantially reduced, i.e. in the metal(0) oxidation state.

Without wishing to be bound by any theory, the role of the metallic nanoparticles in the dihydrogen sensing application is to chemisorb $H_2$ and transfer the adsorbed hydrogen species for oxidation on the semiconductive metal oxide. The metallic nanoparticles may thus have the capacity to form metal hydride species when exposed to $H_2$. A wide range of metallic nanoparticles are reported to be suitable for such purposes, and the invention in its most general form is not limited to specific metallic compositions. In some embodiments, the metallic nanoparticles comprise at least one metal selected from the group consisting of palladium (Pd), platinum (Pt), magnesium (Mg) and nickel (Ni). In some embodiments, the metallic nanoparticles are selected from the group consisting of Pd, Mg, $LaNi_5$, $ZrV_2$, FeTi, $Mg_2Ni$ and $TiV_2$ nanoparticles; these metals and alloys are known for their capacity to chemisorb $H_2$ and form metal hydrides. In some embodiments, the metal nanoparticles are Pd or Pd alloy nanoparticles.

The metallic nanoparticles are preferably uniformly decorated over the surface of the crystalline semiconductive metal oxide layer. Suitable loadings and particle sizes of the metallic nanoparticles will depend on the metal oxide layer composition and structure as well as the type of metallic nanoparticles used. In the case of Pd nanoparticles on a micro-structured $TiO_2$ metal oxide layer, a loading of 28 atom % Pd, as measured by energy dispersive X-ray spectroscopy (EDS), has been found to provide good performance. As will be explained hereafter, the metal oxide layer may be decorated with suitably sized metallic nanoparticles by electroless plating techniques.

As seen in FIG. 1, chemiresistive substrate 100 comprises Pd nanoparticles 110 on $TiO_2$ layer 102. Nanoparticles 110 are formed both on micro-shells 104 and on base plane 106 of the $TiO_2$ layer.

Method of Producing a Dihydrogen-Sensitive Chemiresistive Substrate

The invention also relates to a method of producing a dihydrogen-sensitive chemiresistive substrate, as generally described above. The method comprises a step of producing a close-packed monolayer array of polymeric microspheres on a support surface. The polymeric microspheres are then etched to reduce the particle size and thus produce an array of spaced apart polymeric microparticles on the support surface. A coating of metal oxide is then deposited over the support surface and the polymeric microparticles, and the coated support surface is calcined to remove the polymeric microparticles and produce a crystalline semiconductive metal oxide layer on the support surface. The resultant metal oxide layer comprises an array of spaced apart hollow metal oxide micro-shells protruding from a base plane of the metal oxide layer. The metal oxide layer is then decorated with metallic nanoparticles to produce the dihydrogen-sensitive chemiresistive substrate.

Producing a Close-Packed Monolayer Array of Polymeric Microspheres

The method involves a step of producing a close-packed monolayer array of polymeric microspheres on a support surface. The support surface may be a mechanically stable substrate made of an insulating material, such as a glass. The substrate may comprise a pair of electrically conductive electrodes, such as interdigitated electrodes, formed on the substrate surface. The monolayer array of polymeric microspheres may be assembled over the electrodes on the support surface.

Polymeric microspheres have previously been used to fabricate close-packed micro/nano-scale features on substrates in a technique known as colloidal lithography. As used herein, polymeric microspheres include both micro- and nano-sized spheres, for example spheres in a size range of from 0.4 micrometers (400 nm) to 10 micrometers. The microspheres may have approximately uniform shapes and sizes. It will be appreciated, however, that perfect monodispersity and sphericity is not required, but the microspheres should be sufficiently uniform and spherical to permit a hexagonal close-packing arrangement. The polymeric microspheres may comprise any suitable polymer, for example but not limited to polystyrene.

Polymeric microspheres may be assembled in a close-packed monolayer array on the support surface by previously reported techniques, including Langmuir-Blodgett deposition and dip coating. In these techniques, the microspheres are at placed at a liquid-gas (typically water-air) interface where they self-assemble into a close-packed hexagonal monolayer configuration. The microspheres are then carefully transferred to the substrate surface. Alternatively, the microspheres may be dropped onto the surface in a solvent so that they self-assemble on the surface.

Optionally, the substrate with close-packed monolayer of polymeric microspheres may be heated, prior to the subsequent etching step, to partially melt the base of the microspheres and thus anchor them to the support surface. This may improve the uniformity of the hexagonal array of etched microparticles, and thus ultimately the metal oxide micro-shells. However, this approach has not been found essential as only minor movement of the polymeric particles has been obtained in the subsequent processing steps. A satisfactory arrangement of spaced apart metal oxide micro-shells can be obtained without the heating step.

Etching the Polymeric Microspheres

The method involves a step of etching the polymeric microspheres to produce an array of spaced apart polymeric microparticles on the support surface. The etching reduces the particle size of the polymeric microspheres so that the microparticles are no longer close-packed, but are instead spaced apart from each other on the support surface. However, the distribution of the microparticles over the surface remains determined, at least to a degree, by the initial close-packed arrangement on the surface. Preferably, the etched microparticles remain substantially in or close to the initial positions of the microspheres, resulting in the formation of a hexagonal array of spaced apart polymeric microparticles.

As used herein, polymeric microparticles include both micro- and nano-sized particles, for example particles in a size range of from 0.2 micrometers (200 nm) to 9 micrometers. The microparticles may remain substantially spherical, or at least retain a substantially circular cross-sectional shape when viewed normal to the plane of the substrate surface. However, it will be appreciated that some irregularity in the shape of the microparticles may be caused by the etching.

The polymeric microspheres may be etched by any technique capable of removing material from the periphery of the microspheres to produce the spaced apart microparticles. Plasma etching has been found to be particularly suitable, but other techniques such as solvent etching are not excluded. Plasma etching involves directing a suitable glow discharge, produced by ionising a gas stream with a high frequency voltage, at the substrate to be etched. The plasma etching may suitably be conducted in a conventional plasma cleaning or plasma etching instrument.

The inventors have found that the degree of etching is an important parameter to be controlled in the method of the invention. If the polymeric microspheres are insufficiently etched, the spacing between the polymeric microparticles may be too small. This can prevent the subsequent deposition of a coherent metal oxide layer encapsulating each individual microparticle while providing good adhesion to the underlying substrate surface. Instead, the deposited metal oxide may bridge multiple polymeric microparticles, leading to a loss of order in the final substrate and/or delamination in the calcination step. If the polymeric microspheres are etched too much, the microparticles will be too small to act as a template in the subsequent metal oxide deposition step.

The degree of etching may be controlled via the process parameters of the etching step. For example, in a plasma etching step, the degree of etching may be controlled via the power used to generate the plasma (e.g. the RF frequency), the plasma flow rate and particularly the etching time. In some embodiments, the etching step is conducted to provide a spacing between the microparticles of at least 0.3 micrometers, or at least 0.5 micrometers.

Coating With a Metal Oxide

The method involves a step of depositing a coating of metal oxide over the support surface and the polymeric microparticles. The metal oxide is generally deposited so that it forms a continuous coating which adopts the configuration provided by the polymeric nanoparticle template. The coating is thus deposited on the support substrate in the regions intermediate the spaced apart microparticles, but extends over and conforms to the shape of the individual polymeric microparticles.

The metal oxide is selected to provide, once calcined, a crystalline semiconductive metal oxide suitable for $H_2$ sensing applications. Suitable metal oxides include, but are not limited to, titanium dioxide ($TiO_2$), zinc oxide (ZnO), tungsten trioxide ($WO_3$) and tin dioxide ($SnO_2$). In some embodiments, the metal oxide is $TiO_2$.

The metal oxide may in principle be deposited by any suitable technique able to provide a thin film of metal oxide over the templated surface. In some embodiments, the metal oxide coating is deposited by chemical vapour deposition (CVD). CVD has been found to provide well-structured continuous coatings and good control of parameters such as coating thickness. However, other low temperature deposition techniques compatible with deposition on polymeric substrates, such as plasma deposition and sputter deposition, are also envisaged.

In some CVD embodiments, the templated substrate is contacted with a hydrolysed metal vapour produced by hydrolysing a suitable metal-containing precursor compound, for example a metal alkyl or metal alkoxide liquid. Where the target metal oxide is $TiO_2$, the precursor compound may be a titanium alkoxide such as titanium isopropoxide. Deposition may be achieved, for example, by positioning the templated surface directly above the precursor compound in a deposition vessel, and passing a stream of humidified gas through the vessel. The precursor compound is thus gradually hydrolysed to form a volatile metal-containing vapour which deposits gradually on the templated surface. Further hydrolysis reactions on the surface ultimately lead to the formation of a metal oxide layer.

The thickness of the metal oxide coating is also an important parameter to control in the method of the invention. If the coating is too thin, it may fragment in the subsequent process steps. On the other hand, if too much metal oxide is deposited, the templated surface may be filled, causing a loss of the desired micro-structured morphology. The thickness of the deposited layer may be controlled, for example, by the deposition time.

The metal oxide coating that is deposited may be amorphous or crystalline. If amorphous, the metal oxide will crystallise in the subsequent calcination step to produce the required crystallinity and semiconductive properties.

Calcining to Produce a Crystalline Semiconductive Metal Oxide Layer

The method involves a step of calcining the coated support surface to remove the polymeric microparticles and produce a crystalline semiconductive metal oxide layer on the support surface. The resultant metal oxide layer comprises an array of spaced apart hollow metal oxide microshells protruding from a base plane of the metal oxide layer.

Calcination generally involves heating the coated support surface to a temperature high enough to remove the polymeric microparticle template. The calcination may be conducted in air or other suitable atmosphere. At the high temperature of calcination, for example above 450° C., or above 500° C., the polymeric microparticles are degraded by combustion and/or pyrolytic mechanisms, with the gaseous by-products escaping through pores in the metal oxide layer. It is proposed that these meso- or macropores facilitate access to the interior of the micro-shells in the ultimate chemiresistive substrate. The calcination may also crystallise the metal oxide layer, thus providing it with semiconductor properties. For example, calcination at 550° C. has been found to produce the crystalline $TiO_2$ anatase phase when the initial $TiO_2$ coating deposited by CVD was amorphous.

The calcination step thus produces a metal oxide layer comprising an array of spaced apart hollow metal oxide micro-shells protruding from a base plane of the metal oxide layer. The metal oxide layer is generally as described herein in the section relating to the chemiresistive substrate.

Decorating the Metal Oxide Layer With Metallic Nanoparticles

The method involves a step of decorating, or functionalising, the metal oxide layer with metallic nanoparticles. The resultant metallic nanoparticles are preferably uniformly distributed over the surface of the crystalline semiconductive metal oxide layer, on both the micro-shells and the base plane. In some embodiments, the metallic nanoparticles comprise at least one metal selected from the group consisting of palladium (Pd), platinum (Pt), magnesium (Mg) and nickel (Ni). In some embodiments, the metallic nanoparticles are selected from the group consisting of Pd, Mg, $LaNi_5$, $ZrV_2$, FeTi, $Mg_2Ni$ and $TiV_2$ nanoparticles. In some embodiments, the metal nanoparticles are Pd or Pd alloy nanoparticles.

The metallic nanoparticles may be produced on the metal oxide layer by a variety of techniques available to the skilled person, and suitable techniques will depend on the type of metallic nanoparticles. In some embodiments, the metallic nanoparticles are produced by electroless plating techniques, in which the micro-structured metal oxide layer is contacted with an electroless bath solution comprising metal salts and a reducing agent. Optionally, the metal oxide layer may first be seeded with a metal seed layer to provide nuclei on which the nanoparticles grow in the bath. Other techniques for producing metallic nanoparticles may include physical vapor deposition techniques and electrodeposition techniques.

Suitable loadings and particle sizes of the metallic nanoparticles for the $H_2$ sensing application may be provided by adjusting the process conditions of the nanoparticle functionalisation step. In the case of Pd nanoparticles on a micro-structured $TiO_2$ metal oxide layer, a loading of 28 atom % Pd, as measured by energy dispersive X-ray spectroscopy (EDS), was achieved by contacting the Pd-seeded $TiO_2$ layer with a basic palladium chloride/hydrazine bath (2.2. mM Pd) for about 20 seconds.

An embodiment of the invention will now be described with reference to FIG. 3, which schematically depicts the preparation of a dihydrogen-sensitive chemiresistive substrate 300. A glass substrate, comprising interdigitated electrodes 304a and 304b, is used as support surface 302. In step 306, a close-packed monolayer of polymeric microspheres 308, arranged in a hexagonal array, is produced on the support surface, for example by dip coating transfer from a self-assembled monolayer at a water-air interface. Microspheres 308 are approximately uniform in size, and have a diameter of about 1.3 micrometers.

In step 310, polymeric microspheres 308 are subjected to plasma etching, which reduces the particle size of resultant polymeric microparticles 312 to about 0.85 micrometers. Spaced apart polymeric microparticles 312 nevertheless remain close to or at their initial positions on support surface 302, so that they remain in a substantially hexagonal array.

In step 314, a continuous coating of $TiO_2$ is deposited over support surface 302 and microparticles 312, the coating conforming to the polymeric microparticle template so that each microparticle is individually encapsulated and the coating is formed directly on the support surface in the regions between the microparticles. The coating is deposited by suspending the templated surface directly above titanium isopropoxide in a deposition vessel, and passing humidified nitrogen through the vessel.

In step 316, the coated support surface is calcined in air at 550° C., producing crystalline $TiO_2$ layer 318 which overlies electrodes 304a and 304b on support surface 302. The removal of the polymeric template results in the formation of spaced apart, hollow $TiO_2$ micro-shells 320 which protrude from, but are integrally formed in, $TiO_2$ layer 318. The hemispherical micro-shells have a diameter of about 1 micrometers, and are thus spaced apart from each other by about 0.35 micrometers. The thickness of $TiO_2$ layer 318 is about 70 nm.

In step 322, the metal oxide layer 318 is decorated with metallic Pd nanoparticles 324 by electroless plating, optionally after first seeding the layer with Pd. The nanoparticles are uniformly decorated over the $TiO_2$ layer, including on micro-shells 320.

Amperometric Gas Sensor

The invention also relates to an amperometric gas sensor. The amperometric gas sensor comprises a pair of electrodes on a support surface, and a chemiresistive substrate arranged over the electrodes on the support surface. The chemiresistive substrate thus electrically connects the electrodes, so that a current can flow through the chemiresistive substrate when a potential difference is applied between the electrodes.

The chemiresistive substrate may generally be according to any of the embodiments disclosed herein. The electrodes and substrate may be of conventional design for sensor applications. For example, the electrodes may be interdigitated.

Figure 3:
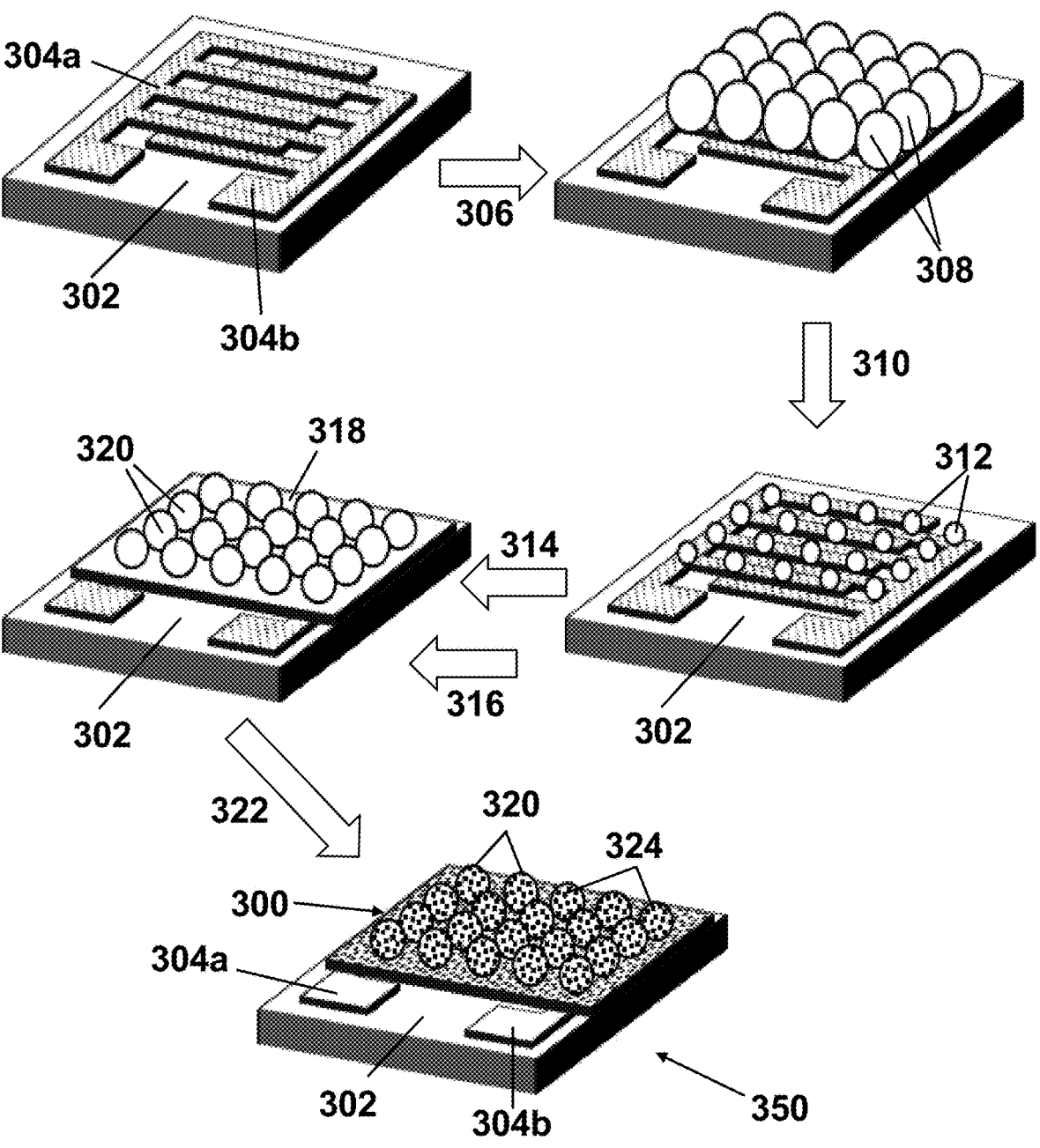
FIG. 3 schematically depicts a method of producing a dihydrogen-sensitive chemiresistive substrate according to an embodiment of the invention.

As seen in FIG. 3, amperometric gas sensor 350 includes interdigitated electrodes 304a and 304b which are disposed on and form part of support surface 302 of a glass substrate. Chemiresistive substrate 300, as described above, is arranged on the surface and in electrical contact with the electrodes.

System for Detecting Dihydrogen in an Oxygen-Containing Gas

The invention also relates to a system for detecting dihydrogen in an oxygen-containing gas. The system comprises an amperometric gas sensor (AGS) as disclosed herein, a power supply to apply a potential difference between the electrodes of the amperometric gas sensor, and a current meter to measure the current flowing between the electrodes through the chemiresistive substrate of the AGS. The AGS may generally be according to any of the embodiments disclosed herein, for example sensor 350 depicted in FIG. 3. The power supply and current meter are conventional accessories for AGS devices, and can be commercially procured.

The system may further comprise a light source to illuminate the chemiresistive substrate of the amperometric gas sensor. The light source emits light having an energy greater than the band gap of the metal oxide in the chemiresistive substrate. Thus, when the chemiresistive substrate is illuminated and exposed to $O_2$ and $H_2$, photoactivation of the semiconductive metal oxide may increase the concentration of surface-activated species which affect the material's conductivity. The sensitivity of the device is thus enhanced. The light source may be an ultraviolet (UV) light source.

In some embodiments, the system further comprises a housing in which the amperometric gas sensor is disposed. The housing may comprise a transparent window to allow illumination of the chemiresistive substrate by the light source. In some embodiments, the system is configured to direct a flow of the oxygen-containing gas through the housing, and over the chemiresistive substrate, to facilitate the detection of $H_2$ therein.

Method of Detecting Dihydrogen in an Oxygen-Containing Gas

The invention also relates to a method of detecting dihydrogen in an oxygen-containing gas. The method comprises exposing the chemiresistive substrate of an amperometric gas sensor, as disclosed herein, to an oxygen-containing gas comprising hydrogen to be detected, applying a potential difference between the electrodes, and measuring the current flowing between the electrodes through the chemiresistive substrate. The chemiresistive substrate may generally be according to any of the embodiments disclosed herein, for example chemiresistive substrate 300 described herein with reference to FIG. 3.

The analyte gas may be any oxygen-containing gas which does or may contain $H_2$, where it may be desirable to detect and/or quantify the $H_2$ content. For example, the gas may be air, with the purpose of the analysis to detect nearby $H_2$ leaks. In another example, the gas may be breath as used in breath diagnostic tests. If the target gas lacks sufficient oxygen, air or oxygen may be added in known amounts to facilitate the detection of $H_2$.

The method is considered applicable to the detection and/or quantification of $H_2$ across a wide range of concentrations, for example in an amount of between 4 ppm and 4 vol %, or between 4 ppm and 1000 ppm. The inventors have demonstrated a limit of detection (LOD) as low as 3.5 ppm and a linear response to $H_2$ concentration spanning the range of 50 to 500 ppm. It is envisaged that the sensor may be useful up to the lower explosive limit of $H_2$ (4 vol % in air) and even higher.

The oxygen-containing gas may comprise one or more contaminant gases, for example one or more of water vapour, carbon dioxide, methyl ethyl ketone, acetone, acetaldehyde and nitric oxide. Due to the excellent $H_2$ selectivity of the chemiresistive substrate, the methods of the invention have been found useful for detecting and quantifying $H_2$ even in the presence of a variety of common interfering gases.

In some embodiments, the potential difference applied between the electrodes is at least 3V, or at least 6V, for example in the range of 6V to 12V, or about 9V. Higher potentials have generally been found to improve the sensitivity of the method.

In some embodiments, the method comprises illuminating the chemiresistive substrate of the amperometric gas sensor with light having an energy greater than the semiconductive metal oxide band gap. For example, the light may be UV light. The intensity of the light may be in the range of 100 to 10000 $\mu W \cdot cm^{-2}$. Higher intensities, for example 2000 $\mu W \cdot cm^{-2}$ or higher, have generally been found to improve the sensitivity of the method.

An advantage of the method is that it may be conducted at low temperatures, particularly when illuminated with activating light. In some embodiments, the chemiresistive substrate is thus maintained at a temperature of below 100° C., or below 50° C. during the method.

The method may involve quantifying the amount of $H_2$ in the oxygen-containing gas. To do this, the amperometric gas sensor may be calibrated with calibration gases of known composition, and a calibration curve (or model) may be developed which relates the current response to the hydrogen concentration in the gas.

EXAMPLES

The present invention is described with reference to the following examples. It is to be understood that the examples are illustrative of and not limiting to the invention described herein.

Materials and Methods

All chemicals utilized in the synthesis were purchased from Sigma-Aldrich and used as received. Interdigitated electrodes fabricated using borofloat glass substrates were acquired from Micrux Technologies. The platinum interdigitated electrodes comprised finger pairs with 10 μm width and 5 μm spacing. The active sensing zone was 3.5 mm in diameter. All substrates used in this study were washed with acetone, ethanol, and milli-Q water then dried under dry nitrogen before use.

A FEISEM Quanta and a FEI Nova NanoSEM was used to conduct scanning electron microscopy (SEM) characterisation. All images were collected using an accelerating voltage of 5 kV and beam current of 50 pA.

The thickness of the prepared $TiO_2$ layer on the substrates was measured using a surface profiler (TencorP-16+).

X-ray photoemission spectroscopy (XPS) analysis was conducted with a thermo K-Alpha XPS equipped with an Al K-Alpha monochromated X-ray radiation source. The samples were prepared on titanium coated silicon substrates. All spectra were background corrected using the Shirley algorithm, and all binding energies (BE) were aligned considering adventitious carbon (C 1 s) having a BE of 285 eV.

A D8 Discover Micro X-ray diffraction (XRD) instrument equipped with a Cu Kα radiation source (40 kV, 40 mA) and a general area detector diffraction system (GADDS) was utilized to study the crystal structure of substrates.

UV-vis spectroscopic analysis was conducted by placing the coated substrate in a cuvette and analysing the substrate with a UV-vis spectrophotometer (Varian Cary 60) in transmittance mode in a 200-800 nm wavelength range.

Example 1

Polystyrene microspheres with a diameter of about 1350 nm were synthesized by a method described in *ACS Appl. Mater. Interfaces* 2015, 7, 1491-1499. Briefly, a 100 ml three neck round bottom flask containing 20 ml ethanol and 200 mg of polyvinylpyrrolidone (PVP) was placed under $N_2$ atmosphere, and 2 ml of styrene was then injected into the flask. The solution was heated at 70° C. and stirred (1000 rpm). A solution of 28 mg of the initiator azobisisobutyronitrile (AIBN) dissolved in 20 ml of ethanol was added to the flask. The polymerization reaction was carried out for 24 hours. The colloidal polystyrene microspheres were washed several times with ethanol and water and dispersed in 40 mL of ethanol.

Figure 4:
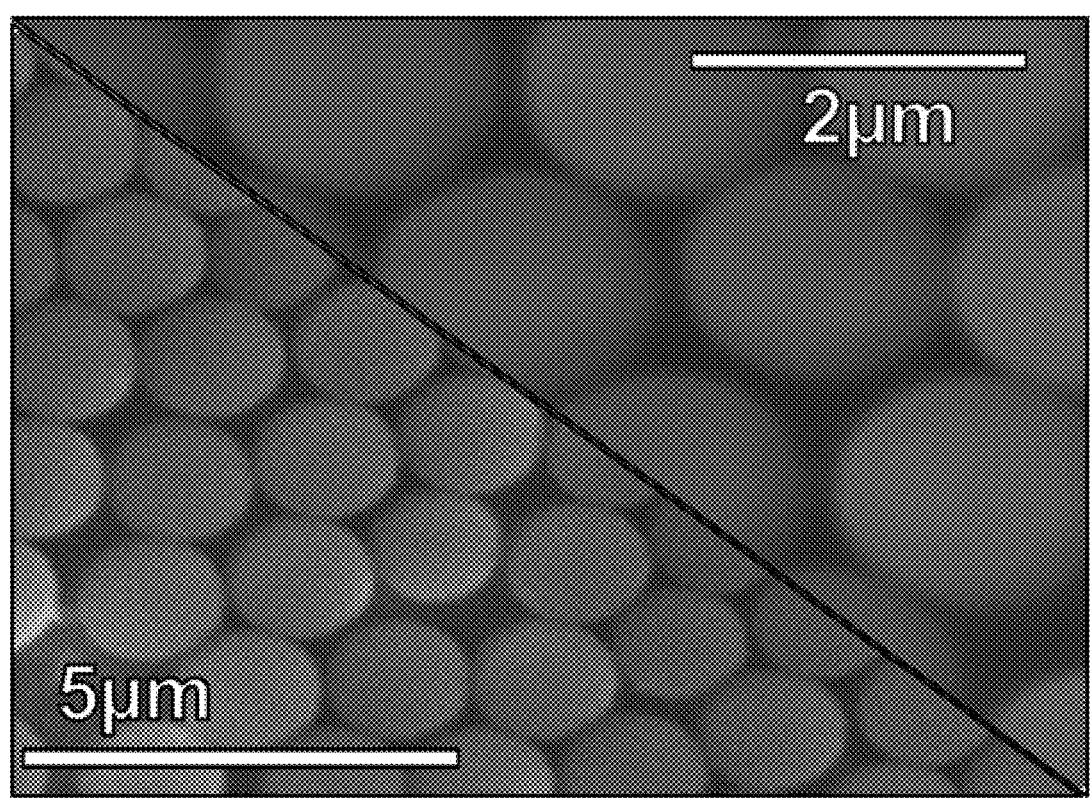
FIG. 4 depicts SEM images of a hexagonally close-packed polystyrene microsphere monolayer on a support surface, as produced in Example 1.

A standard petri-dish containing 3 mM of sodium hydroxide (NaOH) solution was used to form a water/air interface. A suspension of the polystyrene microspheres was injected into the surface to approximately fill the interface, followed by 10 μL of sodium dodecyl sulfate (SDS) solution to compact the interface by modifying the surface tension. This process resulted in a closely packed hexagonal monolayer that was then transferred onto the sensor substrates from the interface by dipping the substrate in the solution and removing it gently over a period of 30 s. The surface was dried to produce a substrate with a hexagonally close-packed polystyrene microsphere monolayer on the surface, as seen in the SEM images shown in FIG. 4.

Figure 5:
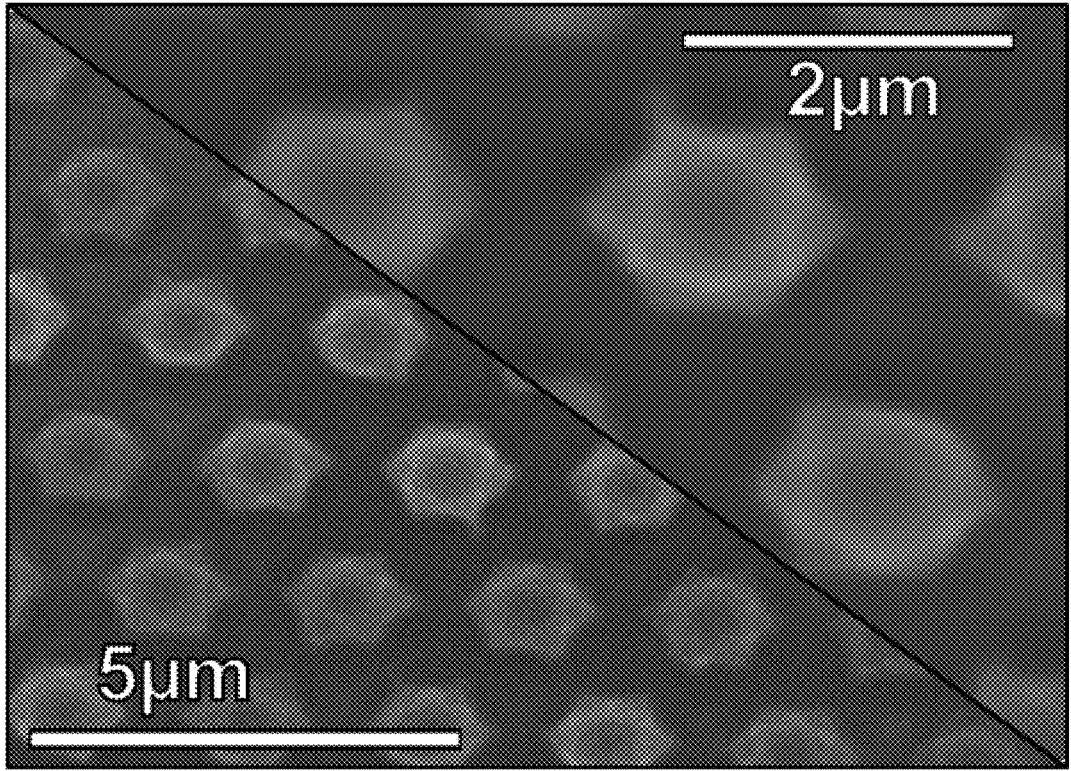
FIG. 5 depicts SEM images of an array of spaced apart polystyrene microparticles present on a support surface after a 20-minute plasma etching step, as produced in Example 1.

Substrates produced in this manner were then etched using a plasma cleaner (Gatan Model 950, RF 50 W, 10 mTorr and 10 sccm gas flow) under pure oxygen for 20 minutes to reduce the polystyrene particle size and form a uniform array of non-closely packed polystyrene microparticles on the surface. SEM images of the substrate are shown in FIG. 5. The hexagonal configuration of the array was substantially retained after the etching.

Figure 6:
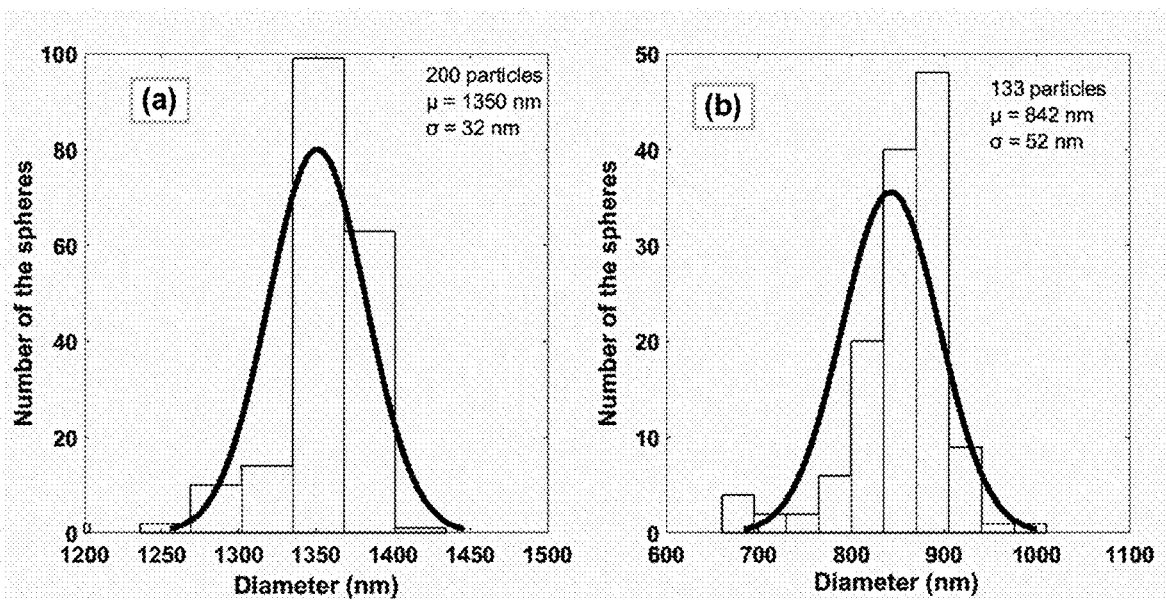
FIG. 6 shows particle size distributions of (a) the close-packed polystyrene microspheres before the etching step, and (b) the spaced apart polystyrene microparticles after the 20-minute etching step, as produced in Example 1.

The polystyrene particle size distribution on the surface before and after etching was estimated with an image processing program based on MATLAB using a Hough Transform, and the results are shown in FIG. 6. The average particle size before etching was calculated as 1350±32 nm, while after etching it was calculated as 842±52 nm.

Example 2

Titanium (IV) isopropoxide (TTIP, 1 ml) was added to a 100 ml round bottom flask, and the assembly was kept at constant temperature of 68° C. under inert atmosphere using $N_2$ gas. The substrate with etched polystyrene microparticle surface array (as prepared in Example 1) was suspended above the TTIP with the polystyrene-templated surface facing downwards. Dry $N_2$ at a rate of 10 standard cubic centimetres per minute (sccm) was passed through 100 ml of milli-Q water in a dreschel bottle, and the resulting water vapor in $N_2$ carrier was flowed through the flask assembly to initiate chemical vapour deposition (CVD) of $TiO_2$ on the substrate surface. The thickness of the deposited layer was controlled by the reaction time. After the desired time (10 minutes), the reaction was ceased by stopping the water vapor flow, introducing dry $N_2$ and removing the heat source to allow the flask to cool to room temperature. The coated substrate was then removed from the flask with a pair of tweezers.

The $TiO_2$-coated substrate was then subjected to a one-step annealing process at 550° C. for 1 hour in air. This crystallised the amorphous $TiO_2$ coating and removed the underlying polystyrene template.

The thickness of the annealed $TiO_2$ layer was determined by placing a control substrate of polished silicon wafer thin film next to the polystyrene-modified substrate during the CVD process and subsequent annealing. Half of the control substrate sample area was covered with photoresist, which was removed (along with its deposited $TiO_2$ layer) through a lift-off process (acetone etching) following the $TiO_2$ coating process. The step-change in surface height on the control substrate, measured by profilometry, thus represented the equivalent thickness of $TiO_2$ deposited on the polystyrene-modified substrate. The standard deviation was calculated using five random points on the step edge of the deposition after removal of the photoresist mask on the control sample. The thickness of the annealed layer of $TiO_2$ was thus determined to be 68±11 nm.

Figure 7:
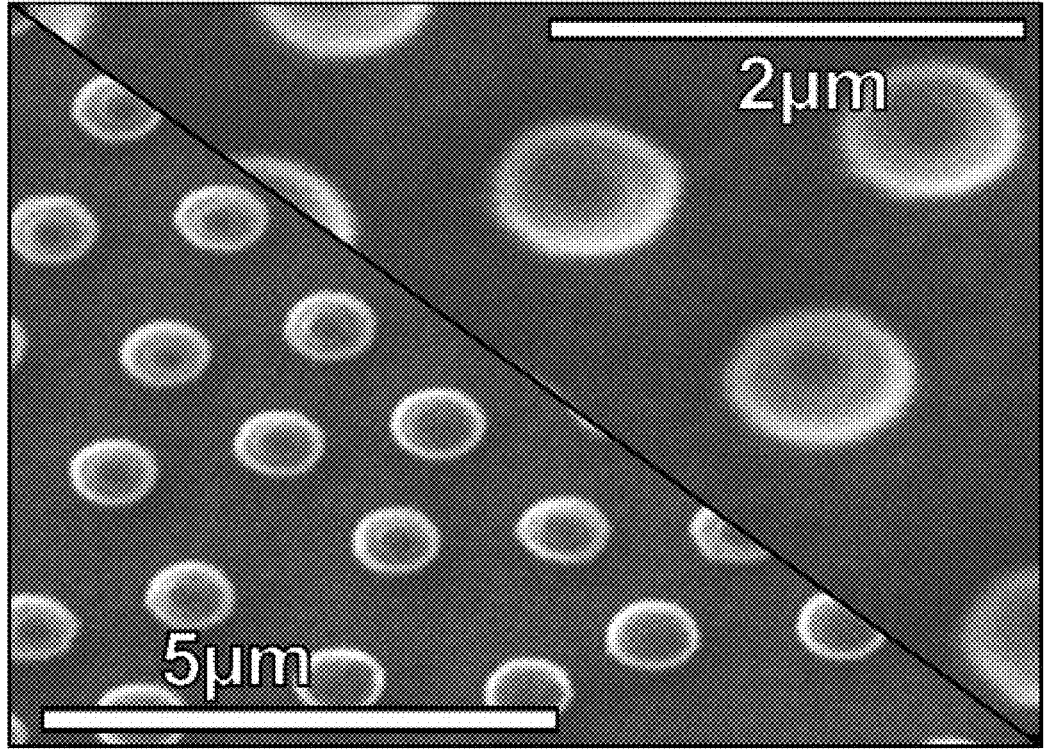
FIG. 7 depicts SEM images of an amorphous $TiO_2$ coating deposited on a polymeric microparticle-templated substrate surface, as produced in Example 2.
Figure 8:
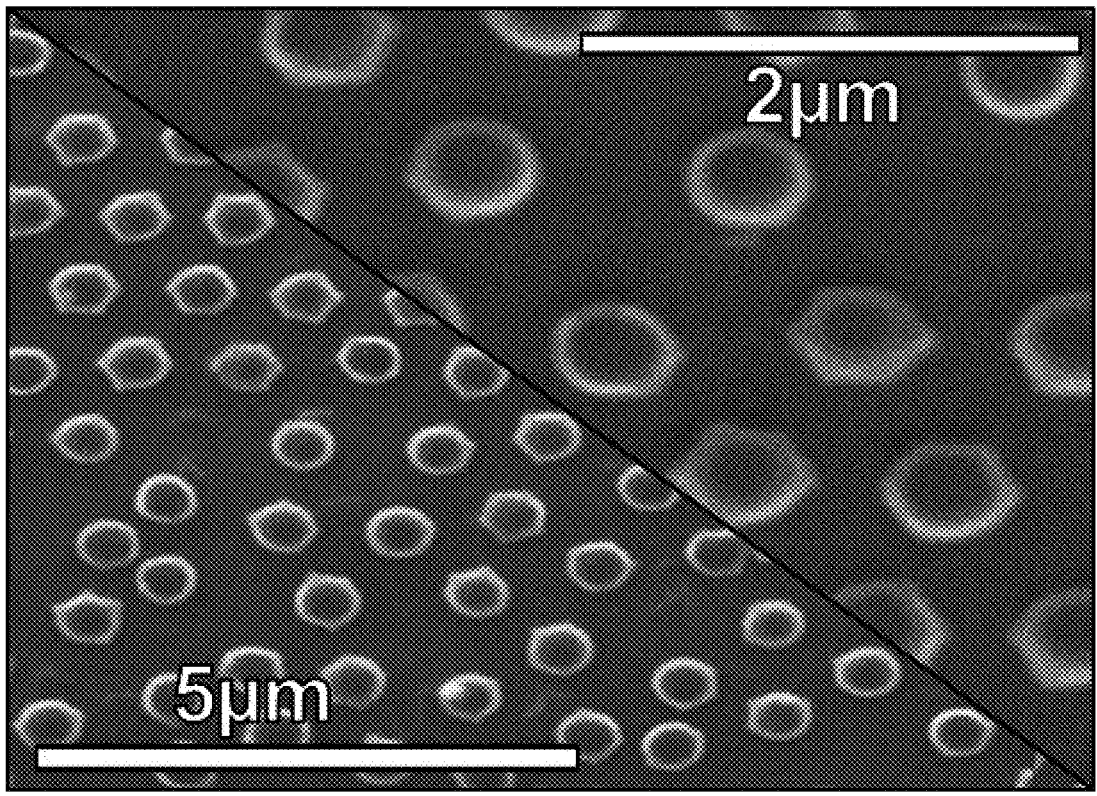
FIG. 8 depicts SEM images of a crystalline $TiO_2$ layer, comprising an array of spaced apart, hollow $TiO_2$ micro-shells, as produced in Example 2.

As can be seen in FIG. 7, the amorphous $TiO_2$ layer formed after CVD was uniformly coated over the surface, including over the uniform array of non-closely packed polystyrene microparticles. This morphology was retained once the polystyrene microparticle template was removed in the annealing step, as seen in FIG. 8. An approximately hexagonal array of uniformly dimensioned and spaced-apart hollow crystalline $TiO_2$ micro-shells thus remained on the $TiO_2$-coated surface. The hollow and porous nature of the micro-shells could be seen in high magnification SEM images, for example as shown in FIG. 2. It was estimated that the average spacing between the micro-shells was about 0.5 micrometers.

Example 3

Figure 9:
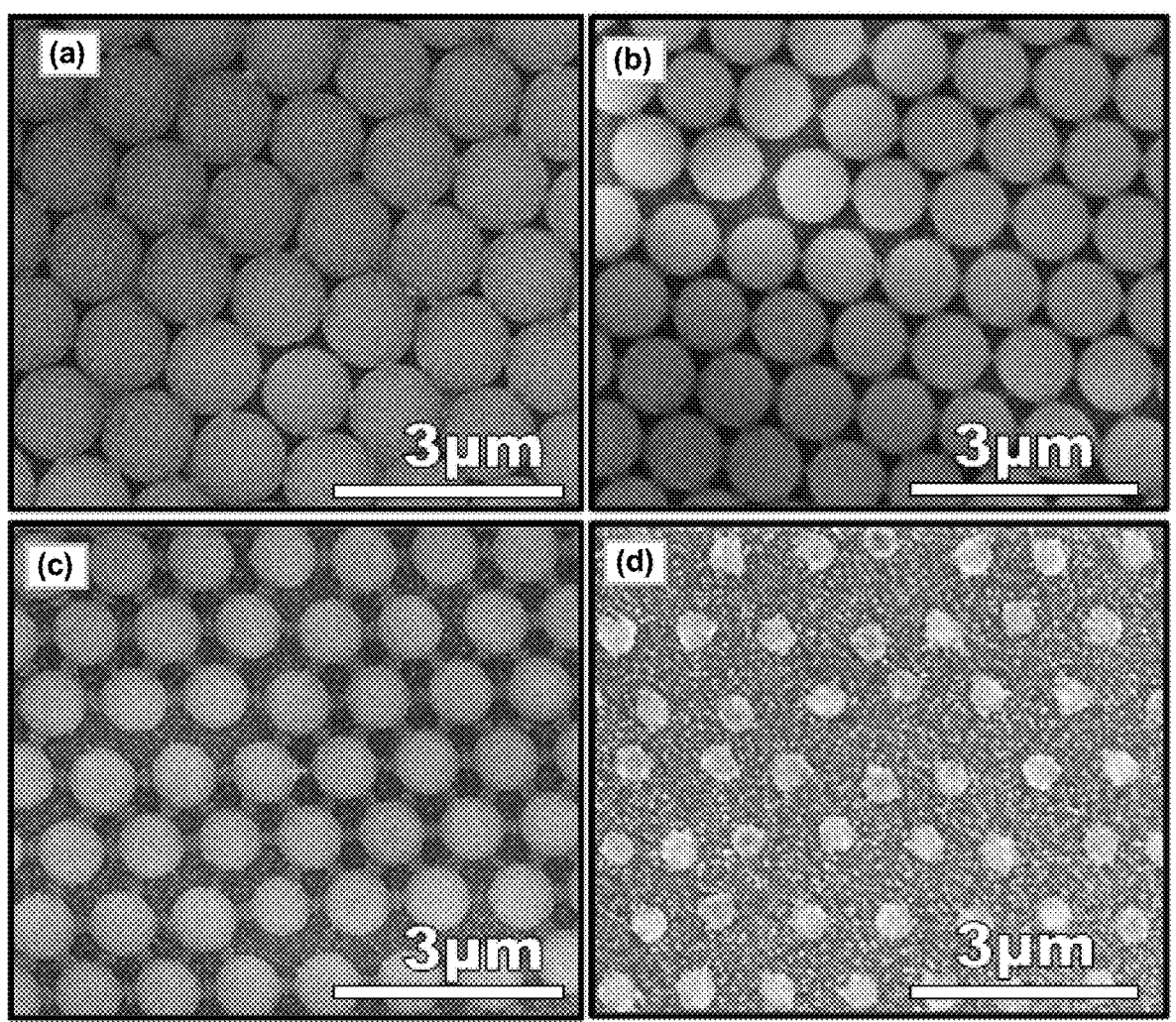
FIG. 9 depicts SEM images of the transformation of (a) a close packed array of polystyrene nanospheres into progressively smaller polystyrene microparticles by plasma etching for (b) 5 minutes, (c) 10 minutes, and (d) 15 minutes, in Example 3.

The effect of polystyrene microparticle size and spacing was investigated by varying the etching time used in the method of Example 1 (but using a higher RF power setting). Etching times of 5, 10 and 15 minutes were used, and SEM images of the resultant substrates (pre-etching, 5, 10 and 15 minutes) are shown in FIG. 9 (a)-(d). The progressive reduction in particle size can be seen.

$TiO_2$ was then deposited on the substrates using the method of Example 2. Without etching, i.e. using the hexagonally close-packed polystyrene surface, the deposited $TiO_2$ layer detached from the substrate during the annealing step. This was ascribed to the different thermal expansion coefficient of $TiO_2$ and the underlying substrate, and the inadequate contact of $TiO_2$ with the underlying substrate due to the close packed and highly curved polystyrene microspheres.

Figures 10, 11:
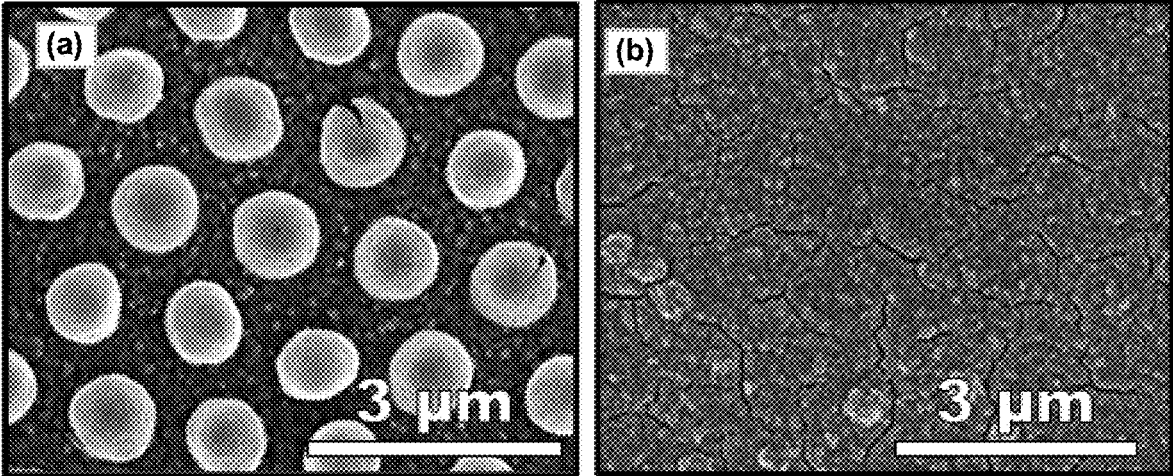
FIG. 10 depicts SEM images of $TiO_2$ coatings deposited by CVD on (a) the close-packed array of polystyrene nanospheres shown in FIG. 9, and on the progressively smaller (b) 5 minute-etched polystyrene microparticles, (c) 10 minute-etched polystyrene microparticles, and (d) 15 minute-etched polystyrene microparticles shown in FIG. 9, as produced in Example 3.
FIG. 11 depicts SEM images of crystalline $TiO_2$ layers produced after (a) a 10 minute CVD deposition time and (b) a 10 minute CVD deposition time, followed by calcination, as produced in Example 4.

When insufficient etching was performed, bridging between individual polystyrene microparticles occurred during CVD, resulting in the formation of randomly distributed isolated islands of porous packed titania after annealing, as shown for etching times of 0, 5 and 10 minutes in FIG. 10 (a)-(c). The extent of bridging decreased with smaller particle sizes. With sufficient etching time, however, the polystyrene microparticles were spaced far enough apart to avoid bridging. As a result, the formation of a microstructured $TiO_2$ surface occurred with little or no disruption in the long-range order, as shown in FIG. 10 (d) for the 15 minute-etched substrate. Under the specific etching conditions used, a 15 min etching time was found to be optimum to produce a well-ordered array of porous hollow micro-shells after the annealing step. Longer etching times will reduce the size of the polystyrene template particles too much and the surface area of the final $TiO_2$ coated substrate would thus be compromised.

Example 4

The effect of $TiO_2$ layer thickness on the resultant surface morphology was also investigated using the method of Example 2 but varying the CVD deposition time. If the deposition time was too short, so that the thickness of the metal oxide layer was less than 50 nm, the deposited layer was too fragile and cracked or fragmented during the annealing. An irregular non-particulate morphology was obtained. If the deposition time was too long, so that the thickness exceeded half the diameter of the etched microparticles, the micro-structured surface was overfilled with $TiO_2$ leading to loss of the microstructure and long-range order on the surface. Under the specific CVD conditions employed, a 10-minute deposition time was found to be optimum, whereas minutes resulted in loss of the desired morphology due to overfilling the surface. The comparison is shown in FIG. 11 (a) and (b).

Example 5

The annealed $TiO_2$-coated substrate prepared in Example 2 was decorated with Pd nanoparticles using a two-step electroless plating (ELP) method. In the first step, a seed layer of Pd was deposited. The substrate was dipped into 2 ml of a solution of tin chloride (2 mM of $SnCl_2$ and 2.5 ml/l of 32% HCl) at room temperature for 5 min, followed by rinsing the substrate in milli Q water for 5 min. The substrate was then dipped in 2 ml of a palladium salt solution (2.5 ml of $Pd(NO_3)_2$ (10 wt. %) and 2.5 ml/l of 70% $HNO_3$) at room temperature for 10 min followed by 5 min rinsing in milli Q water. This procedure was repeated ten times to form a Pd seed layer.

In the second step, the Pd-seeded substrate was transferred into an electroless plating bath (2.2 mM of $PdCl_2$, 20 mM of $Na_2$-EDTA, 40 ml/l of $NH_3 \cdot H_2O$ (30%), 1.1 ml/l of $N_2H_4$ (1M), at pH=10) for a deposition period of 20 seconds at a constant temperature of 60° C. Then the substrate was rinsed with milli Q water and dried overnight at 120° C.

SEM images of the Pd-seeded substrate did not show any visible Pd nanoparticles due to the small particle size, but nanoparticles distributed uniformly over the substrate were clearly visible after the electroplating step as seen in FIG. 1. The $TiO_2$-coated substrates before Pd seeding, after seeding and after electroless deposition were also studied using energy dispersive X-ray spectroscopy (EDS). The EDS results confirmed the presence of Pd on the surface, in an amount of 1.1 wt. % (5 atom %) for the seeded sample and 7.8 wt. % (28 atom %) in the electroplated sample with Pd-nanoparticles.

The size and distribution of the Pd nanoparticles was found to be dependent on, and controllable by, the electroplating time in step 2. For example, a 60 second contact time in step 2 resulted in a high loading of Pd on the surface (19.3 wt. % by EDS).

Example 6

The method of Examples 1 and 2 was used to produce a micro-structured $TiO_2$ surface with an array of uniformly dimensioned and spaced-apart hollow crystalline $TiO_2$ micro-shells on a quartz substrate. Quartz was selected to allow UV-vis analysis. The method of example 5 was then used to seed the surface with Pd and subsequently to decorate with Pd nanoparticles.

Figure 12:
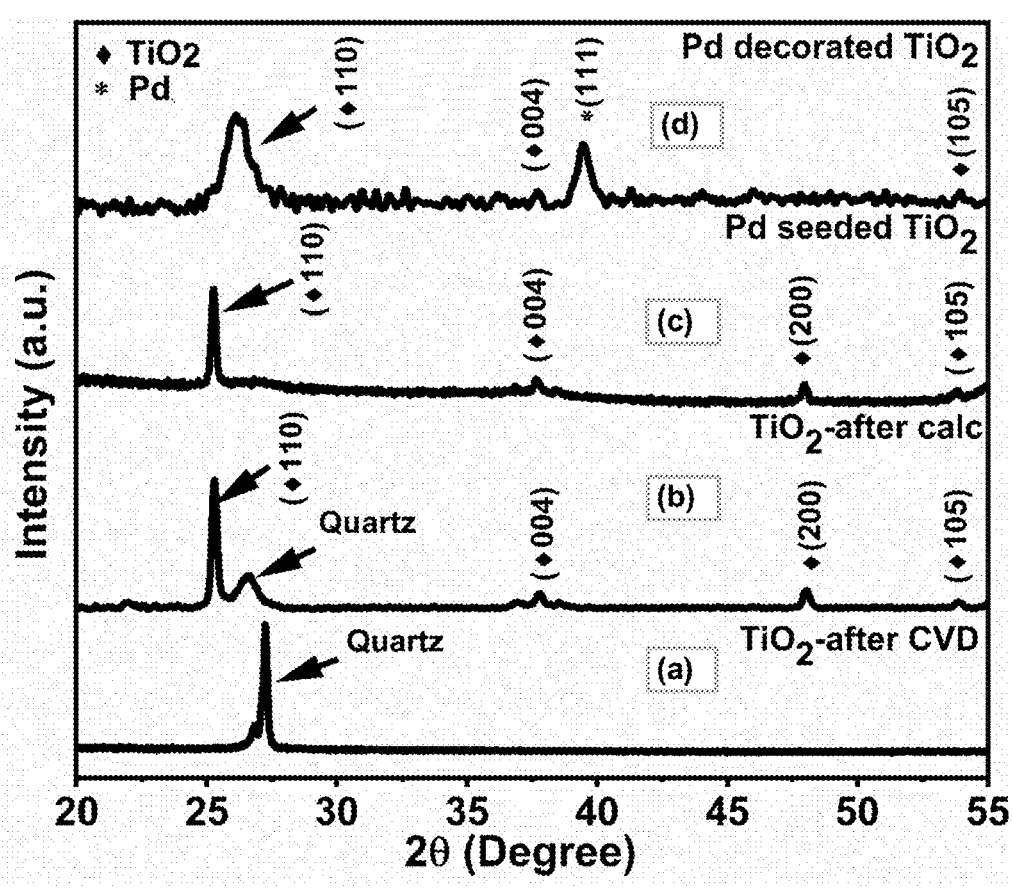
FIG. 12 shows XRD patterns of the $TiO_2$ coated substrates (a) after the $TiO_2$ CVD deposition step, (b) after calcination, (c) after Pd seeding, and (d) after decoration with Pd nanoparticles by electroless plating, as produced on a quartz substrate in Example 6.

The substrates were characterized with XRD and FIG. 12 shows the XRD patterns: (a) after the CVD deposition step, (b) after annealing, (c) after Pd seeding, and (d) after electroless Pd plating. Amorphous $TiO_2$ was formed after CVD, but annealing caused crystallisation: distinct peaks were indexed for (101), (004), (200), and (105) planes of the $TiO_2$ crystal anatase. The Pd seeded substrate showed no visible Pd peaks due to the small particle size and/or the low Pd content. After electroless plating, a peak corresponding to that expected for the (111) plane of Pd nanoparticles was observed.

Figure 13:
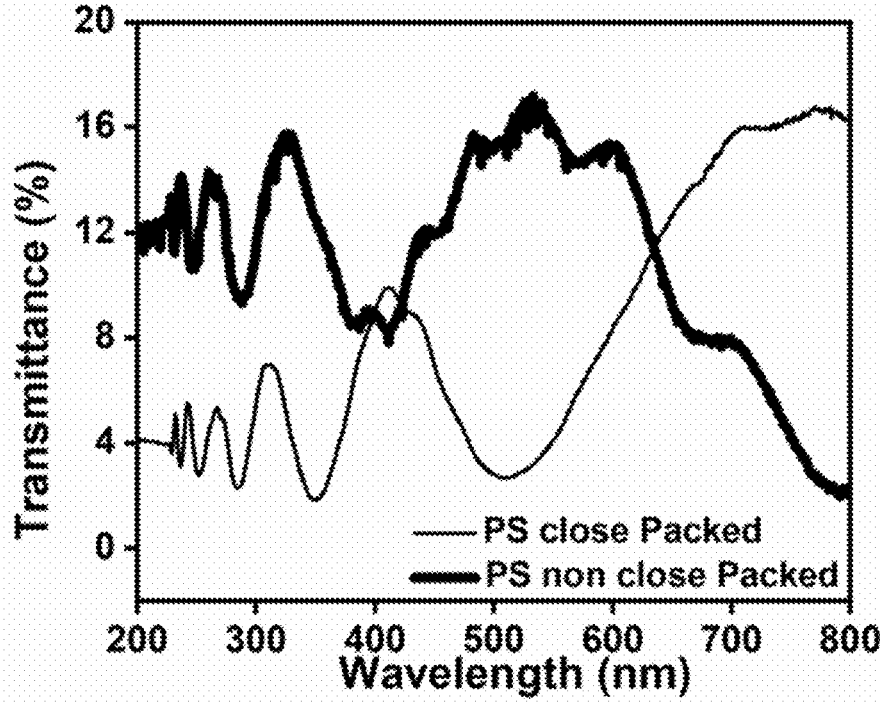
FIG. 13 shows UV-vis transmission spectra of the arrays of hexagonally close-packed polystyrene microspheres and etched, spaced apart polystyrene microparticles, as produced on a quartz substrate in Example 6.

UV-vis analysis was performed on the quartz substrate after deposition of the close-packed hexagonal array of polystyrene microspheres, and after etching to reduce the polystyrene particles size. The results are shown in FIG. 13. Since the close-packed polystyrene microspheres were arranged as an ordered hexagonal array on the surface, the substrate acts as a photonic crystal. The transmittance thus shows wave features in the spectrum which are attributed to light interacting with the periodic structure of the nano-array. After the plasma etching process, the size of polystyrene particles was reduced and the interparticle distances correspondingly increased. Nevertheless, the array retains long range order as can be seen from the wave pattern in the transmittance spectrum.

Figure 14:
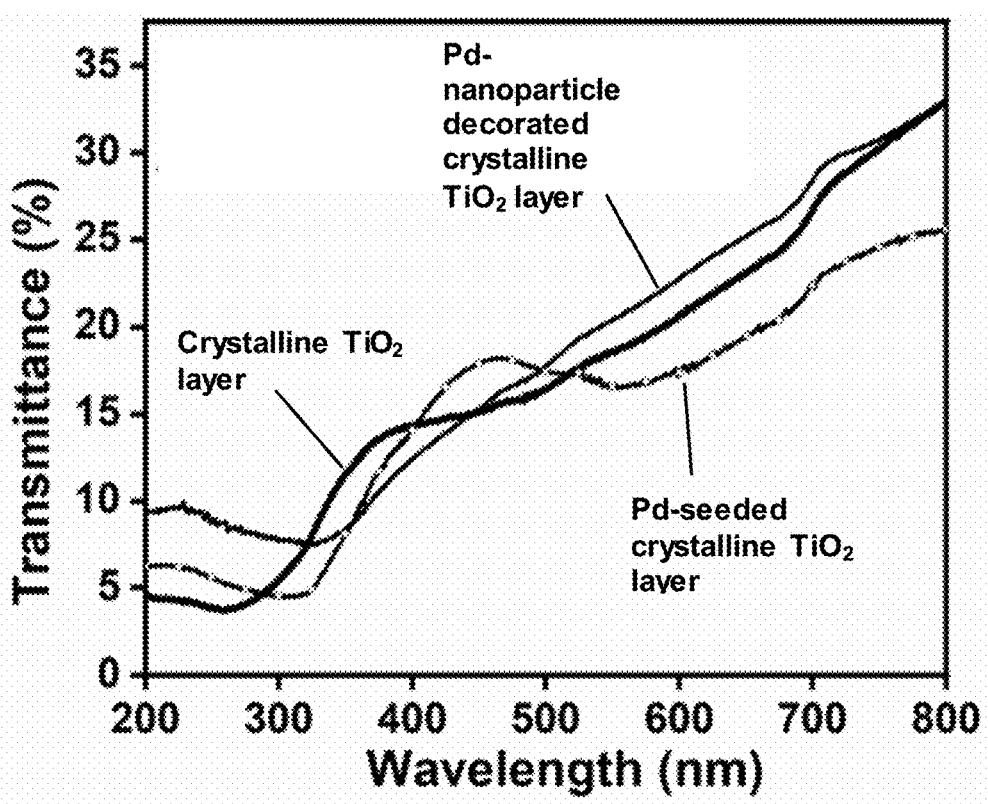
FIG. 14 shows UV-vis transmission spectra of the micro-structured crystalline $TiO_2$ layer after calcination, after Pd-seeding and after decoration with Pd nanoparticles by electroless plating, as produced on a quartz substrate in Example 6.
Figure 15:
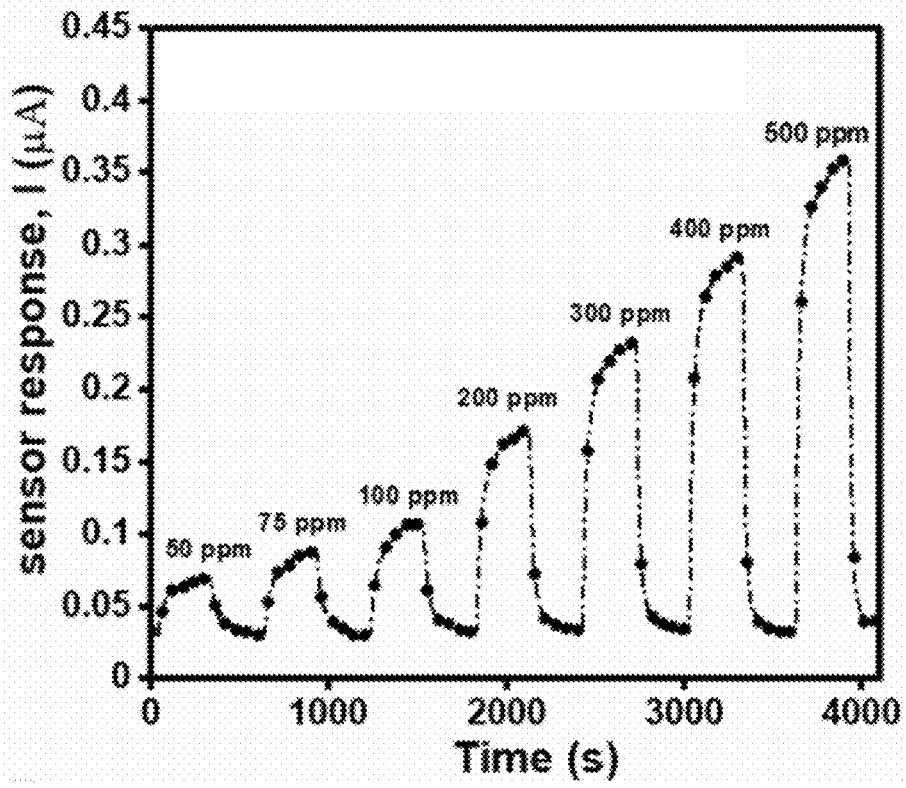
FIG. 15 shows the absolute current response of the amperometric gas sensor produced in Example 5, at 9V bias and 365 nm UV illumination with an intensity of 2024 $\mu W \cdot cm^{-2}$, to a range of $H_2$ concentrations, as obtained in Example 7.

As seen in FIG. 14, after $TiO_2$ deposition and annealing the substrate exhibits an absorption edge at about 380 nm (3.26eV) which is associated with the formation of wide band gap $TiO_2$ layer. A red shift in the absorption spectrum after seeding and decoration with Pd was observed; this is ascribed to the Pd nano-crystallites acting as sensitizers for capturing a large number of visible-light photons.

Example 7

Sensor substrates to be evaluated in $H_2$ sensing applications were mounted in a custom-made Teflon test chamber with an internal ceramic heating bed and an in-built optically polished quartz window to allow light activation. The electrodes of the sensors were connected to the terminals of a power supply unit, with the circuit configured to allow current measurement with an ammeter at constant applied potential. An Agilent E3631, a triple output DC power supply was used to apply the target potential bias to the sensor and to provide thermal excitation to the ceramic heater. The sensor responses were measured using an Agilent 34411A (6 ½ digital multimeter) and stored using a data acquisition computer. A UV LED source (Edmon Optics) with wavelength of 365 nm was used for photoactivation of the substrate at a maximum intensity of 2024 $\mu W \cdot cm^{-2}$. The intensity of the light was adjustable to 108, 562, 945, 1496 and 2024 $\mu W \cdot cm^{-2}$, with the light intensity calibrated using a PM16-40 power meter from THORLABS. The sensors were exposed to $H_2$ concentrations ranging from to 500 ppm (balance of dry air) while keeping the total gas flow rate at 200 sccm. A computer controlled multichannel mass flow controller (MFC) system was utilized to control the gas flow rate and the concentration of hydrogen.

The sensors were thus investigated as amperometric gas sensors by applying different bias (0.1, 3, 6 and 9 V), with and without illumination by the UV light, and measuring the resultant current. The operating temperature of the sensor was maintained at 33° C. for the duration of all tests. A baseline was established before each different test condition of bias and light intensity by exposing the substrate to a flow of dry air for 2 hours before introducing $H_2$. The response magnitude ($\Delta I$) for the test condition was defined as the difference between the output current under the specified $H_2$ gas exposure period ($I_g$) and that in air ($I_a$): $\Delta I = I_g - I_a$.

Figure 16:
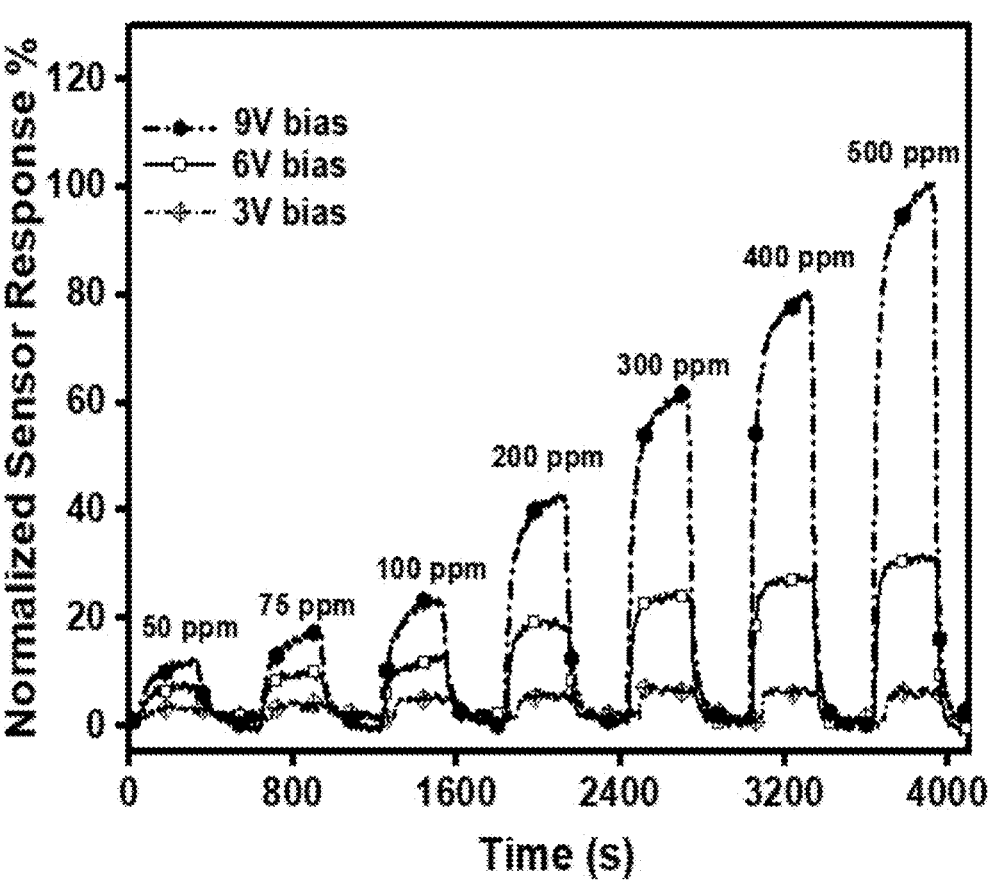
FIG. 16 shows the normalised current response of the amperometric gas sensor produced in Example 5, at 3V, 6V and 9V bias and 365 nm UV illumination with an intensity of 2024 $\mu W \cdot cm^{-2}$, to a range of $H_2$ concentrations, as obtained in Example 7.
Figure 17:
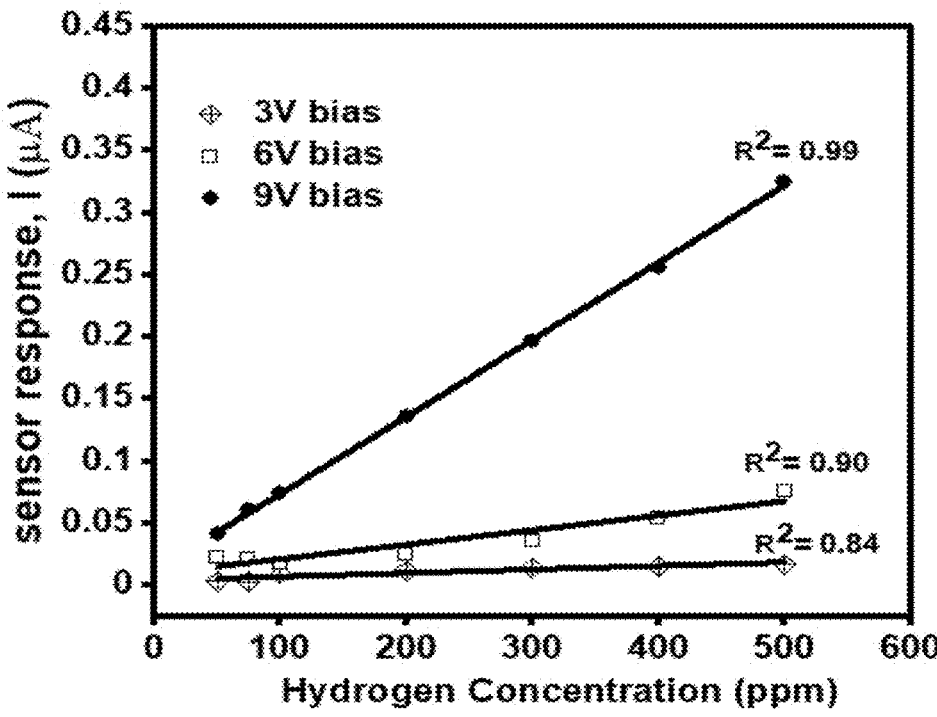
FIG. 17 shows linear calibration curves fitted to the sensor response against hydrogen concentration at 3V, 6V and 9V bias under UV illumination, as obtained in Example 7.

The micro-structured $TiO_2$-coated sensor substrate decorated with Pd nanoparticles, as produced in Example 5 (20 second electroplating contact time), was evaluated under 3V, 6V and 9V bias and light illumination at 365 nm with an intensity of 2024 $\mu W \cdot cm^{-2}$. The absolute current response with the 9V bias is shown in Figure and the normalised response (100% at 500 ppm) for the three bias values are compared in FIG. 16. The sensor provided an excellent response to the $H_2$ concentration, with the greatest sensitivity at higher bias. A calibration curve for the three bias conditions are shown in FIG. 17. A highly linear response of current to $H_2$ concentration was evident, particularly at 6V and 9V base (R 2 values of 0.90 and 0.99 for the fits, respectively). The sensor produced no detectable response at very low bias, e.g. 0.1V.

Figures 18, 19:
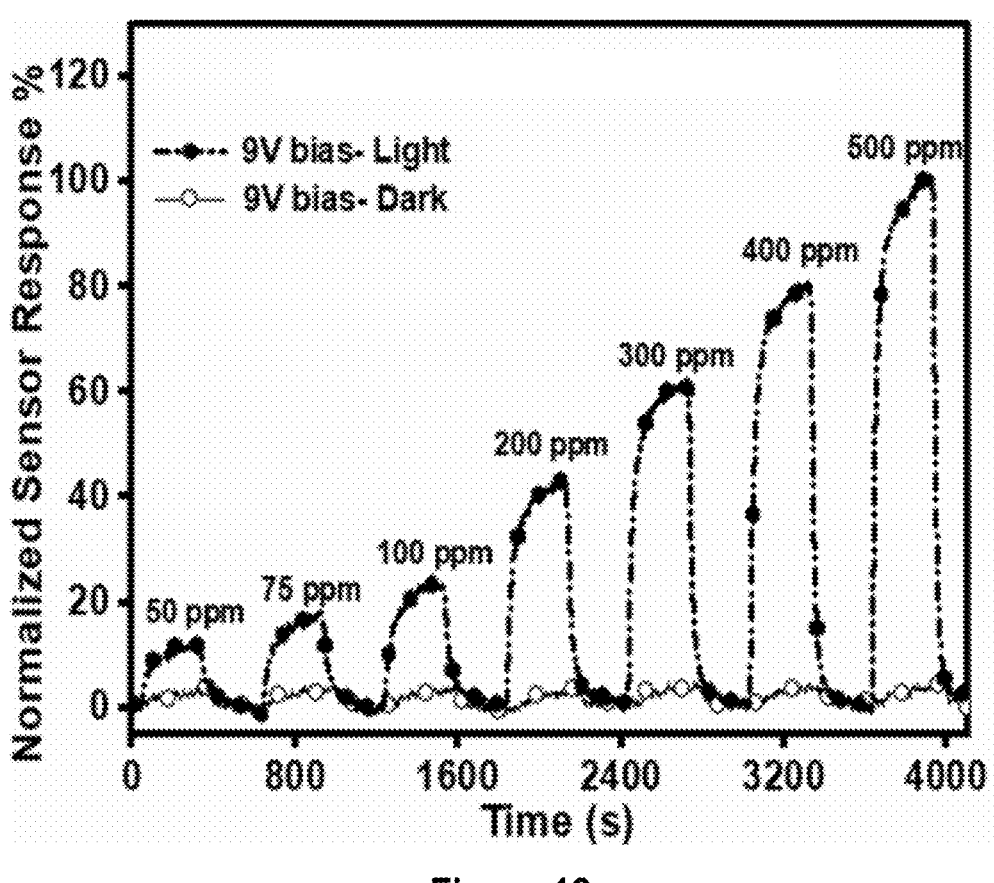
FIG. 18 shows the normalised current response of the amperometric gas sensor produced in Example 5, at 9V bias and under either dark conditions or under UV illumination with an intensity of 2024 $\mu W \cdot cm^{-2}$, to a range of $H_2$ concentrations, as obtained in Example 7.
FIG. 19 shows the normalised current response of the amperometric gas sensor produced in Example 5, at 9V bias and at different intensities of UV illumination, to 500 ppm $H_2$, as obtained in multiple repeat analyses in Example 7.

The micro-structured $TiO_2$-coated sensor substrate decorated with Pd nanoparticles, as produced in Example 5, was again evaluated at 9V bias but without illumination (dark conditions). The results, with comparison against the response under illumination (365 nm/intensity of 2024 $\mu W \cdot cm^{-2}$) are shown in FIG. 18. A response to $H_2$ concentration is still evident, but the sensitivity of the device is greatly reduced without illumination.

The sensitivity of the device at each condition was calculated from the slope of the best fit calibration curves. For example, at 9V bias under UV illumination the sensitivity was S=6.2 $\mu A$/ppm. The limit of detection (LoD) of the sensors towards $H_2$ under the different test conditions was determined using three standard deviations of the sensor response output toward a $H_2$-free blank sample (i.e. dry air). The response time, $t_{90}$-res, was calculated as the time needed for the sensor signal to reach 90% of the final change in signal. The recovery time, $t_{90}$-rec, was calculated as the time needed for the sensor signal to return 90% of the way to the baseline signal. The LoD, signal to noise ratio (SNR), response time, recovery time and sensitivity results are shown in Table 1.

TABLE 1

| Condition | SNR | LoD (ppm) | $t_{90}$-res (s) | $t_{90}$-rec (s) | Sensitivity ($\mu A$/ppm) |
|---|---|---|---|---|---|
| 3 V, 33° C., UV light | 3.8 | 14.5 | 15 | 18 | 1.6 |
| 6 V, 33° C., UV light | 18 | 6.21 | 36 | 21 | 2.9 |
| 9 V, 33° C., UV light | 72 | 3.52 | 45 | 24 | 6.2 |
| 9 V, 33° C., no UV light | 0.006 | — | — | — | — |

The response of the device in the experiment at 9V bias and illumination at intensity of 2024 $\mu W \cdot cm^{-2}$ was calculated according to the formula R (%)=($R_{H2}-R_{air}$)/$R_{air} \times 100$, where $R_{air}$ is the current of the sensor in the presence of dry air and $R_{H2}$ is the current when the sensor is exposed to $H_2$. The results shown in Table 2 demonstrate that the sensor response increases when the $H_2$ concentration increases.

TABLE 2

| $H_2$ concentration | Response (%) |
|---|---|
| 50 | 55.4 |
| 75 | 65 |

TABLE 2-continued

| $H_2$ concentration | Response (%) |
|---|---|
| 100 | 70.2 |
| 200 | 80.4 |
| 300 | 84.3 |
| 400 | 88 |
| 500 | 91 |

The micro-structured $TiO_2$-coated sensor substrate decorated with Pd nanoparticles, as produced in Example 5, was again evaluated under 9V bias but in this series the intensity of the UV illumination was varied while maintaining the $H_2$ concentration constant at 500 ppm. The normalised intensity response results, with five sequential repeats at each condition, are shown in FIG. 19. The sensor response decreased with the decrease in illumination intensity. Higher intensity illumination is expected to generate relatively more electron-hole pairs and thus photo-induced oxygen ions on the surface. The higher concentration of these species increases the magnitude of the response toward $H_2$ gas. The results also show the excellent repeatability of the response at 9V bias and constant illumination at 365 nm with an intensity of 2024 $\mu W \cdot cm^{-2}$.

Figure 20:
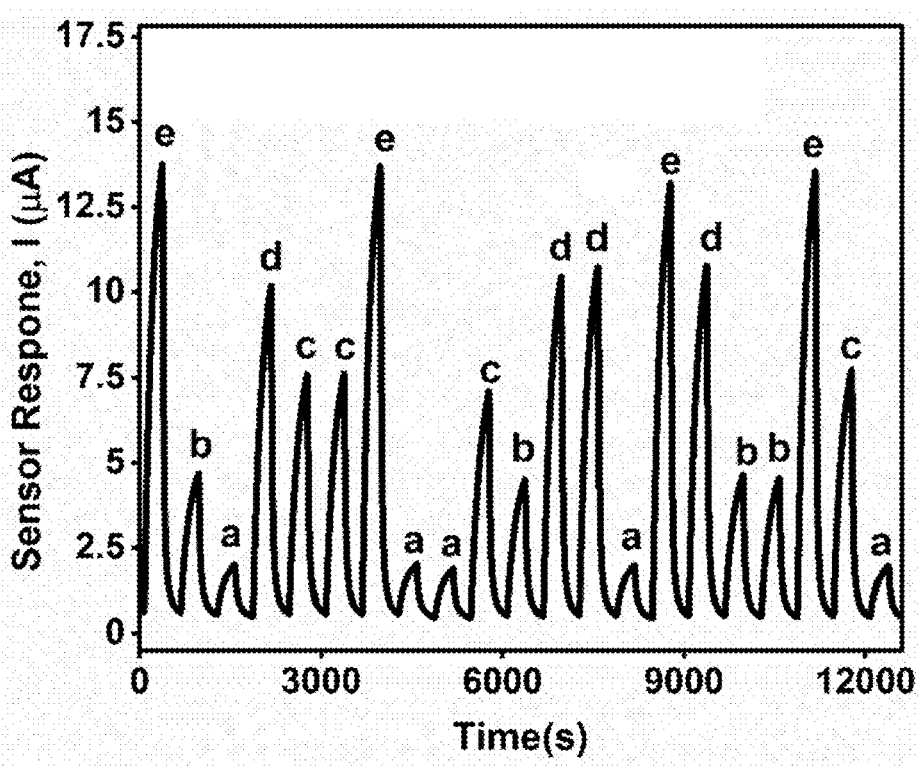
FIG. 20 shows the absolute current response of the amperometric gas sensor produced in Example 5, at 9V bias and under 365 nm UV illumination with an intensity of 2024 $\mu W \cdot cm^{-2}$, to a test sequence of different $H_2$ concentrations, as obtained in Example 7.
Figure 21:
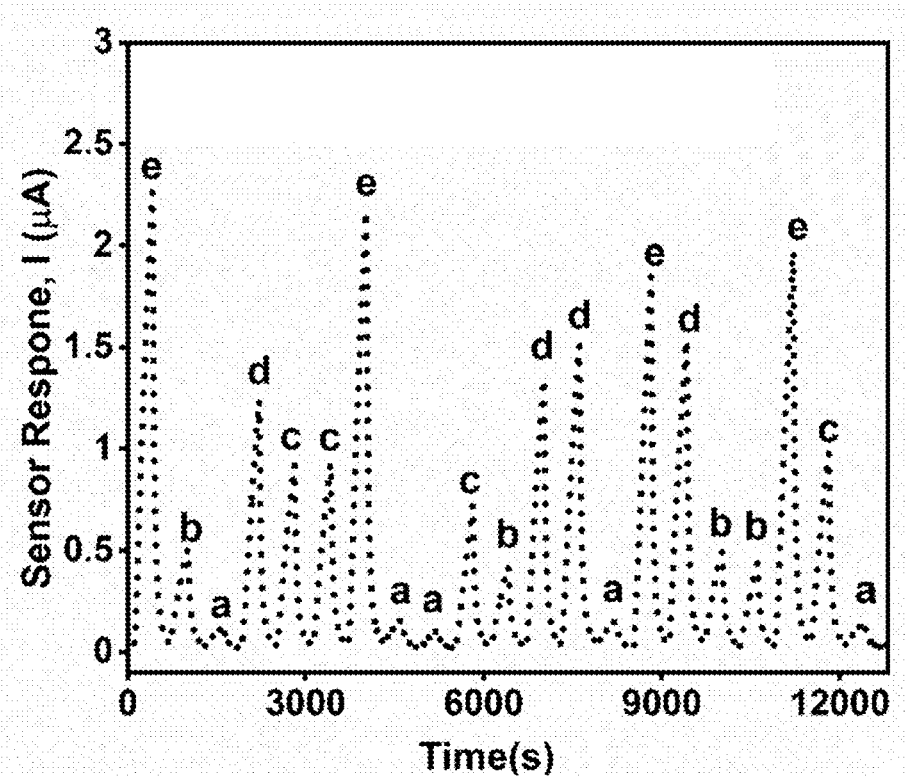
FIG. 21 shows the absolute current response of the amperometric gas sensor produced in Example 5, at 9V bias and dark conditions, to a test sequence of different $H_2$ concentrations, as obtained in Example 7.

The same sensor substrate was also used to investigate whether the response was affected by a previous sensing event, i.e. whether there was any memory effect. A test sequence was developed with five different hydrogen gas concentrations (designated a, b, c, d and e); which are a=100 ppm, b=200 ppm, c=300 ppm, d=400 ppm, and e=500 ppm. The sequence was designed so that each concentration was repeated a minimum of four times and each concentration was followed at least once by each of the other four tested concentrations. The sensor response results at 33° C. with light illumination (365 nm with an intensity of 2024 $\mu W \cdot cm^{-2}$) and without illumination are shown in FIGS. 20 and 21 respectively. The co-efficient of variance (CoV) and repeatability were calculated for each condition according to the formula $CoV$ $(\%) = \sigma/x^- \times 100\%$ and repeatability $(\%) = 100\% - CoV$ (%), where $\sigma$ is the standard deviation and $x^-$ is the mean. The results are shown in Table 3. No memory effect was evident in the results; very high repeatability was obtained under both illumination conditions.

TABLE 3

| | Repeatability (n = 4) | | | | |
|---|---|---|---|---|---|
| | a (100 ppm) | b (200 ppm) | c (300 ppm) | d (400 ppm) | e (500 ppm) |
| No illumination | 99.2 | 99.5 | 99.0 | 99.3 | 99.1 |
| UV illumination | 99.8 | 99.9 | 99.7 | 99.5 | 99.7 |

Example 8

The precursor substrates, including the micro-structured $TiO_2$-coated sensor substrate produced in Example 3 (before Pd addition) and the Pd-seeded substrate produced in Example 5 (before the electroless plating step to form nanoparticles) were also evaluated as amperometric gas sensors by the method of Example 7. Thus, different biases (0.1, 3, 6 and 9 V), with and without illumination by the UV light (at 365 nm with an intensity of 2024 $\mu W \cdot cm^{-2}$) were used. No detectable response toward $H_2$ in the evaluated concentration range (50-500 ppm) was obtained. The results confirm the role of the metallic nanoparticles in facilitating $H_2$ chemisorption, dissociation and/or spillover on the chemiresistive substrate surface.

The substrate loaded with large amounts of Pd in Example 5 (9.6 wt. % Pd, 60 seconds electroplating contact time) was also evaluated. A poor sensor response was obtained in this case, demonstrating that excessive loading of metal onto the micro-structured $TiO_2$ substrate should be avoided.

Example 9

Figure 22:
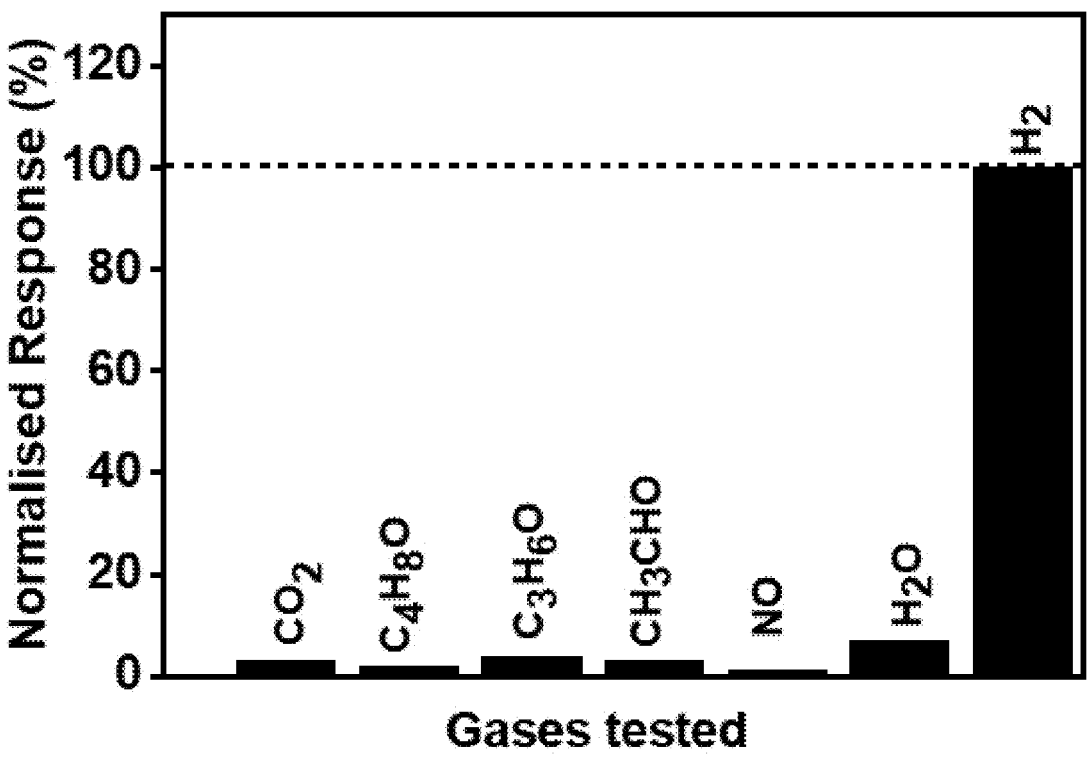
FIG. 22 shows the normalised current response of the amperometric gas sensor produced in Example 5, at 9V bias and under 365 nm UV illumination with an intensity of 2024 $\mu W \cdot cm^{-2}$, to 500 ppm $H_2$ and to a range of different contaminant gases, as obtained in Example 9.

The selectivity of the micro-structured $TiO_2$-coated sensor substrate decorated with Pd nanoparticles, as produced in Example 5 (20 second electroplating contact time), was investigated by exposing the surface to a variety of industrially relevant gases at the following concentrations: carbon dioxide (500 ppm), methyl ethyl ketone (26.1 ppm), acetone (25 ppm), acetaldehyde (3034 ppm) and nitric oxide (2000 ppm). The method of Example 7 was used, except that the gas under investigation was added with the MFC instead of $H_2$. The response of the sensor at 9V bias to the various gases, with comparison to that of $H_2$, is shown in FIG. 22 (illumination at 365 nm with an intensity of 2024 $\mu W \cdot cm^{-2}$) and FIG. 23 (not illuminated). The results demonstrate a high degree of selectivity towards $H_2$ under both conditions.

It is proposed that the balance of selectivity and sensitivity can be controlled by varying the illumination intensity, thus allowing accurate analysis across a wide range of conditions (low ppm to percentage range $H_2$ concentrations, and varying concentrations of other gases). For example, operating the sensor without illumination may enable detection of higher concentrations of $H_2$ (up to the lower explosive limit, LEL, or higher) without substantial response to the cross-interferent gases.

Figure 23:
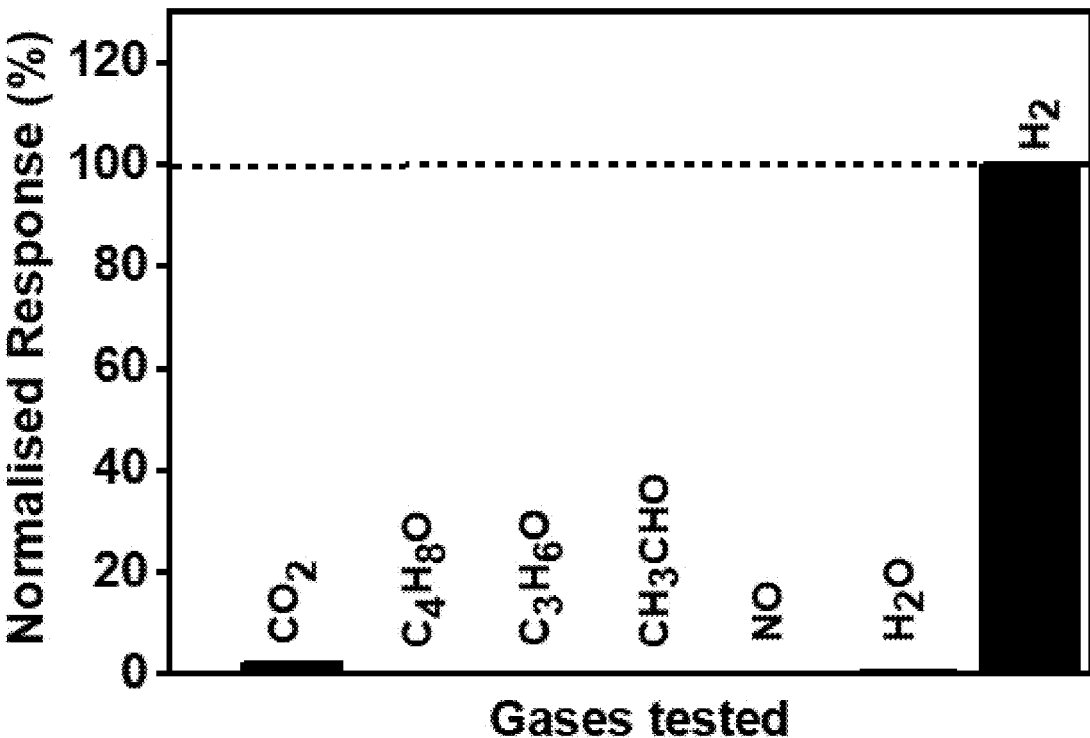
FIG. 23 shows the normalised current of the amperometric gas sensor produced in Example 5, at 9V bias and dark conditions, to 500 ppm $H_2$ and a range of different contaminant gases, as obtained in Example 9.

The effect of humidity on $H_2$ selectivity was also investigated, using 20% relative humidity (RH) as the test condition (0.5 $g/m^3$ $H_2O$). The results are also shown in FIGS. 22 and 23. The sensor shows a significant response to water, particularly under illumination. It is expected that the adsorption of water vapor releases electrons into the depletion layer, resulting in decreased resistance and increased current. Physisorption of $H_2O$ molecules on the oxide surface could also hinder hydrogen chemisorption and dissociation. Nevertheless, the selectivity was still an acceptable 93% to $H_2$ (at 500 ppm) compared to water (at 20% RH).

Example 10

Figure 24:
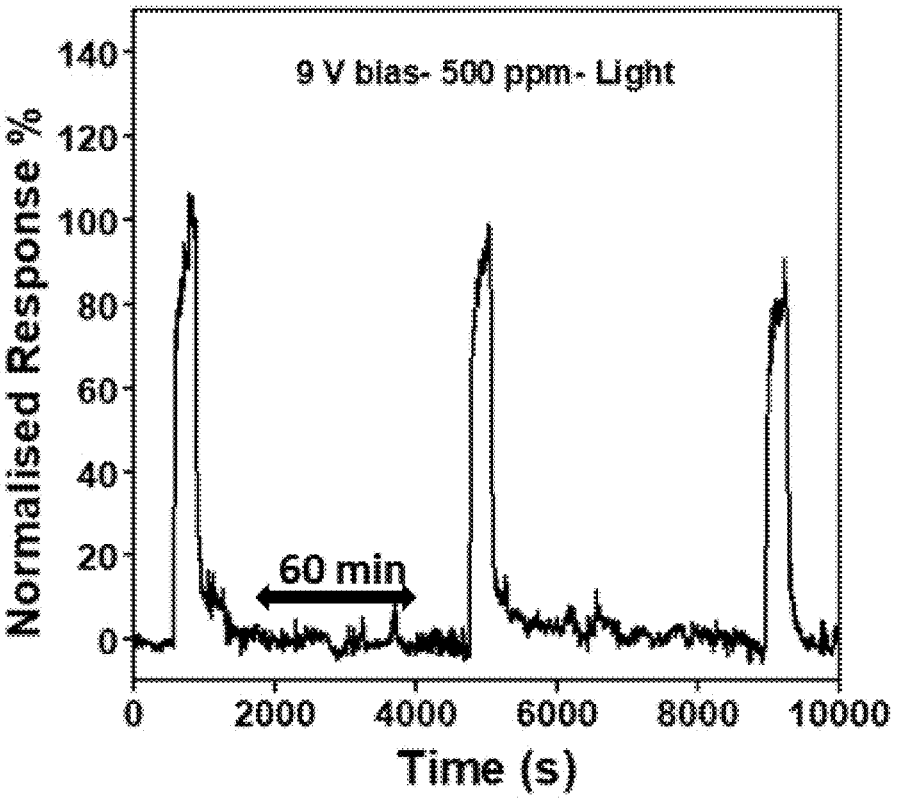
FIG. 24 shows the normalised current response of the amperometric gas sensor produced in Example 5, at 9V bias and under 365 nm UV illumination with an intensity of 2024 $\mu W \cdot cm^{-2}$, to intermittent pulses of $H_2$ at a concentration of 500 ppm, as obtained in Example 10.

In some safety-related applications, a $H_2$ sensor must be able to rapidly detect a sudden spike in $H_2$ concentrations in a gas stream which typically has zero or very low $H_2$ concentration. The micro-structured $TiO_2$-coated sensor substrate decorated with Pd nanoparticles, as produced in Example 5 (20 second electroplating contact time), was thus subjected to a continuous flow of synthetic air with intermittent pulses of $H_2$ to a concentration of 500 ppm $H_2$ (equivalent to 1.25% of the lower explosive limit of $H_2$ in air), with the gas monitored by the method of Example 7. The response of the sensor at 9V bias (illumination at 365 nm with an intensity of 2024 $\mu W \cdot cm^{-2}$) is shown in FIG. 24. The sensor is highly responsive, indicating its suitability for safety-related applications.

Example 11

Figure 25:
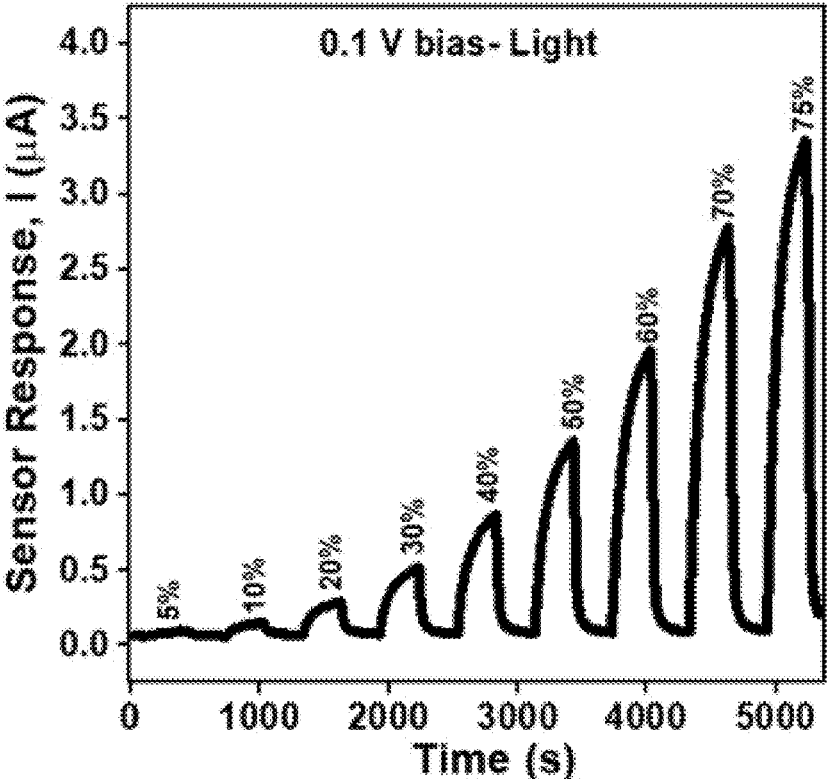
FIG. 25 shows the absolute current response of the amperometric gas sensor produced in Example 5, at 0.1V bias and under 365 nm UV illumination with an intensity of 2024 $\mu W \cdot cm^{-2}$, to a range of $H_2$ concentrations, as obtained in Example 11.

$H_2$ can be combusted in a wide range of concentrations in air (4-75%), and in some applications it is therefore necessary to quantify the concentration of $H_2$ at high concentrations. The sensitivity of the micro-structured $TiO_2$-coated sensor substrate decorated with Pd nanoparticles, as produced in Example 5 (20 second electroplating contact time), was thus further investigated in the range if 5 to 75% $H_2$ concentration. The method of Example 7 was used, except that the feed gas was supplied at $H_2$ concentrations of 5, 10, 20, 30, 40, 50, 60, 70 and 75% (balance of dry air) at 33° C. and total gas flow rate at 200 sccm, with a return to air (0% $H_2$) in between test conditions. At 0.1V bias, no response was detected without illumination. Under illumination at 365 nm with an intensity of 2024 $\mu W \cdot cm^{-2}$, an excellent sensor response was obtained, as seen in FIG. 25.

Figure 26:
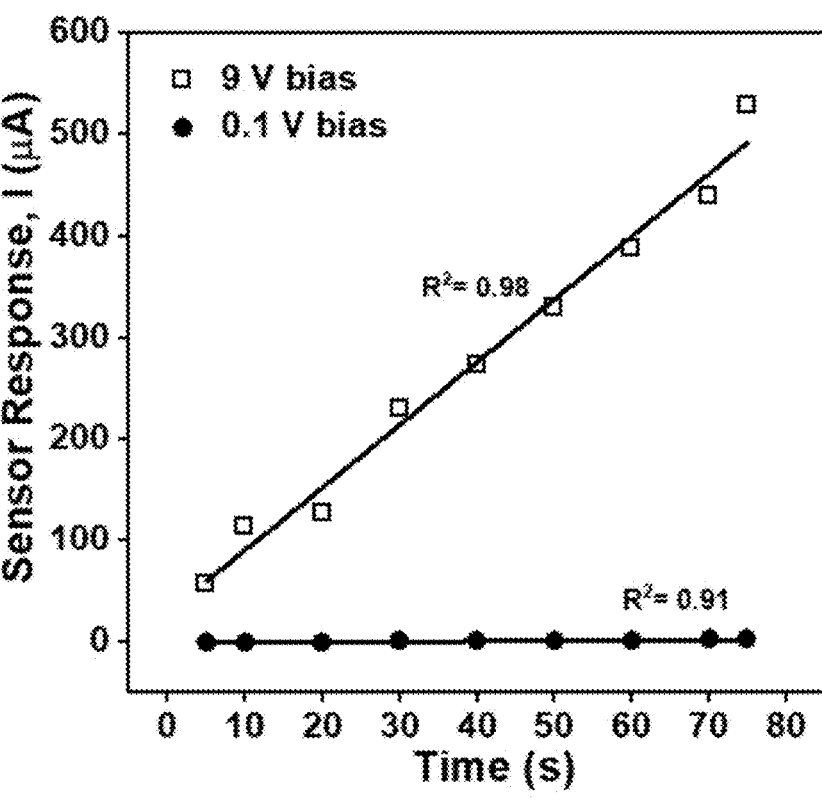
FIG. 26 shows linear calibration curves fitted to the sensor response against hydrogen concentration at 0.1V and 9V bias under UV illumination with an intensity of 2024 $\mu W \cdot cm^{-2}$, as obtained in Example 11.

At high concentrations of $H_2$, a low bias (such as 0.1V) is sufficient to obtain a good current response. However, the sensitivity of the analysis can be further improved by increasing the bias. Calibration curves for the current response as a function of $H_2$ concentration are shown in FIG. 26, for biases of 0.1V and 9V. At the higher bias, the sensitivity increases to 6.2 $\mu A$/ppm with an excellent fit ($R^2 > 0.98$).

Figure 27:
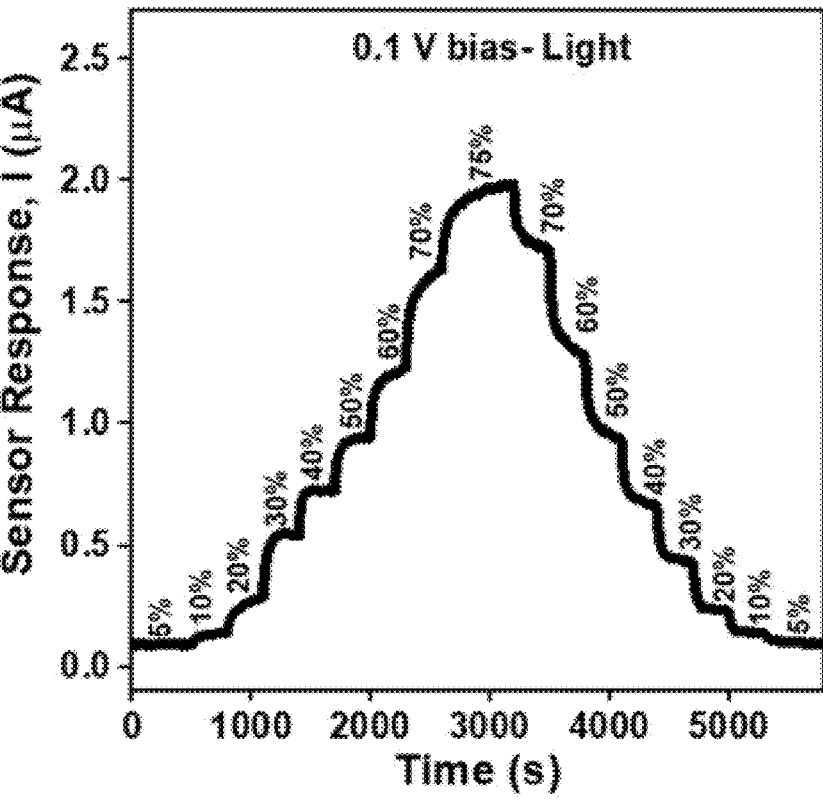
FIG. 27 shows the absolute current response of the amperometric gas sensor produced in Example 5, at 0.1V bias and 365 nm UV illumination with an intensity of 2024 $\mu W \cdot cm^{-2}$, to a continuous flow of $H_2$-containing gas with varying $H_2$ concentration, as obtained in Example 11.

In another experiment, the sensor was exposed to a continuous flow of $H_2$-containing gas with varying $H_2$ concentration from 5 to 75%, without regenerating the sensor at 0% $H_2$ between each different test condition. As seen in FIG. 27, the sensor response magnitude changed significantly in response to the incremental variations in $H_2$ concentration, demonstrating the suitability for continuous monitoring of $H_2$ in a high concentration range. The results demonstrate that $H_2$ sensing can be performed continuously with excellent sensitivity and reproducibility, without any significant memory effects, and without needing to regenerate the sensor as the $H_2$ concentration varies.

Those skilled in the art will appreciate that the invention described herein is susceptible to variations and modifications other than those specifically described. It is understood that the invention includes all such variations and modifications which fall within the spirit and scope of the present invention.

The invention claimed is:

1. A chemiresistive substrate for a dihydrogen-sensitive amperometric gas sensor, the chemiresistive substrate comprising:
  a crystalline semiconductive metal oxide layer comprising an array of spaced apart hollow metal oxide micro-shells protruding from a base plane of the metal oxide layer; and
  metallic nanoparticles decorating the metal oxide layer, wherein the metal oxide micro-shells are spaced apart from their nearest neighbors by a distance of at least 0.2 micrometers.

2. A chemiresistive substrate according to claim 1, wherein the metal oxide is titanium dioxide ($TiO_2$).

3. A chemiresistive substrate according to claim 1, wherein the metallic nanoparticles comprise at least one metal selected from the group consisting of palladium, platinum, magnesium and nickel.

4. A chemiresistive substrate according to claim 1, wherein the metal oxide micro-shells are substantially hemispherical and wherein the metal oxide micro-shells have substantially uniform dimensions.

5. A chemiresistive substrate according to claim 1, wherein the metal oxide micro-shells have a diameter in the range of 0.1 to 2 micrometers.

6. A chemiresistive substrate according to claim 1, wherein the array is a substantially hexagonal array.

7. A chemiresistive substrate according to claim 1, wherein the metal oxide layer has a thickness of between about 40 nm and about 100 nm.

8. An amperometric gas sensor for detecting dihydrogen, comprising:
  a pair of electrodes on a support surface; and
  a chemiresistive substrate according to claim 1 arranged over the electrodes on the support surface.

9. A system for detecting dihydrogen in an oxygen-containing gas, the system comprising:
  an amperometric gas sensor according to claim 8;
  a power supply to apply a potential difference between the electrodes; and
  a current meter to measure the current flowing between the electrodes through the chemiresistive substrate.

10. A system according to claim 9, further comprising a light source to illuminate the chemiresistive substrate of the amperometric gas sensor with light having an energy greater than the metal oxide band gap.

11. A method of detecting dihydrogen in an oxygen-containing gas, the method comprising:
  exposing the chemiresistive substrate of an amperometric gas sensor according to claim 8 to a gas, wherein the gas is an oxygen-containing gas comprising hydrogen;
  applying a potential difference between the electrodes; and
  measuring the current flowing between the electrodes through the chemiresistive substrate.

12. A method according to claim 11, further comprising illuminating the chemiresistive substrate of the amperometric gas sensor with light having an energy greater than the metal oxide band gap.

13. A method according to claim 12, wherein the gas further comprises one or more contaminant gases selected from water vapour, carbon dioxide, methyl ethyl ketone, acetone, acetaldehyde and nitric oxide.

14. A method of producing a dihydrogen-sensitive chemiresistive substrate, the method comprising:
  producing a close-packed monolayer array of polymeric microspheres on a support surface;
  etching the polymeric microspheres to produce an array of spaced apart polymeric microparticles on the support surface;
  depositing a coating of metal oxide over the support surface and the polymeric microparticles;
  calcining the coated support surface to remove the polymeric microparticles and produce a crystalline semiconductive metal oxide layer on the support surface, the metal oxide layer comprising an array of spaced apart hollow metal oxide micro-shells protruding from a base plane of the metal oxide layer; and
  decorating the metal oxide layer with metallic nanoparticles.

15. A method according to claim 14, wherein the metal oxide is titanium dioxide (TiO2) and wherein the metallic nanoparticles comprise at least one metal selected from the group consisting of palladium, platinum, magnesium and nickel.

16. A method according to claim 14, wherein the microspheres are etched by plasma etching.

17. A method according to claim 14, wherein the polymeric microparticles are spaced apart by at least 0.3 micrometers.

18. A method according to claim 14, wherein the coating of metal oxide is deposited over the support surface and polymeric microparticles by chemical vapour deposition.

19. A method according to claim 14, wherein the support surface comprises a pair of electrodes, and the metal oxide layer is produced over the electrodes on the support surface.

* * * * *